(12) United States Patent
Offen et al.

(10) Patent No.: US 10,744,162 B2
(45) Date of Patent: Aug. 18, 2020

(54) GENETICALLY MODIFIED MUSCLE CELLS WHICH EXPRESS NEUROTROPHIC FACTORS

(71) Applicants: RAMOT AT TEL-AVIV UNIVERSITY LTD., Tel-Aviv (IL); YEDA RESEARCH AND DEVELOPMENT CO. LTD., Rehovot (IL)

(72) Inventors: Daniel Offen, Tel-Aviv (IL); Michal Dadon-Nachum, Kfar-Saba (IL); Tali Ben-Zur, RaAnana (IL); Eldad Melamed, Tel-Aviv (IL); David Yaffe, Givat Brenner (IL)

(73) Assignees: RAMOT AT TEL-AVIV UNIVERSITY LTD., Tel-Aviv (IL); YEDA RESEARCH AND DEVELOPMENT CO. LTD., Rehovot (IL)

( * ) Notice: Subject to any disclaimer, the term of this patent is extended or adjusted under 35 U.S.C. 154(b) by 0 days.

(21) Appl. No.: 16/353,680

(22) Filed: Mar. 14, 2019

(65) Prior Publication Data
US 2019/0201452 A1 Jul. 4, 2019

Related U.S. Application Data

(60) Continuation of application No. 15/180,152, filed on Jun. 13, 2016, now abandoned, which is a division of application No. 14/002,782, filed as application No. PCT/IB2012/050976 on Mar. 1, 2012, now Pat. No. 9,365,828.

(60) Provisional application No. 61/448,712, filed on Mar. 3, 2011.

(51) Int. Cl.
| | |
|---|---|
| *A01N 63/00* | (2020.01) |
| *C12N 5/071* | (2010.01) |
| *A61K 35/34* | (2015.01) |
| *C12N 5/077* | (2010.01) |
| *A61K 38/18* | (2006.01) |
| *A61K 38/30* | (2006.01) |
| *A61K 35/12* | (2015.01) |
| *A61K 38/00* | (2006.01) |

(52) U.S. Cl.
CPC .......... *A61K 35/34* (2013.01); *A61K 38/185* (2013.01); *A61K 38/1866* (2013.01); *A61K 38/30* (2013.01); *C12N 5/0658* (2013.01); *C12N 5/0659* (2013.01); *A61K 35/12* (2013.01); *A61K 38/00* (2013.01); *C12N 2501/105* (2013.01); *C12N 2501/13* (2013.01); *C12N 2501/165* (2013.01); *C12N 2510/00* (2013.01)

(58) Field of Classification Search
CPC .............. C12N 5/0658; C12N 5/0659; C12N 2501/105; C12N 2501/13; C12N 2501/165; C12N 2510/00; A61K 38/185; A61K 38/1866; A61K 38/30; A61K 35/12; A61P 25/00
See application file for complete search history.

(56) References Cited

U.S. PATENT DOCUMENTS

| | | |
|---|---|---|
| 2003/0161814 A1 | 8/2003 | Wang et al. |
| 2005/0238625 A1 | 10/2005 | Chancellor et al. |
| 2013/0344041 A1 | 12/2013 | Offen et al. |

FOREIGN PATENT DOCUMENTS

WO     2012117373 A1     9/2012

OTHER PUBLICATIONS

Communication Pursuant to Article 94(3) EPC dated Apr. 18, 2016 From the European Patent Office Re. Application No. 12711003.9.
International Preliminary Report on Patentability dated Sep. 12, 2013 From the International Bureau of WIPO Re. Application No. PCT/IB2012/050976.
International Search Report and theWritten Opinion dated Jul. 2, 2012 From the International Searching Authority Re. Application No. PCT/IB2012/050976.
Official Action dated Oct. 16, 2015 From the US Patent and Trademark Office Re. U.S. Appl. No. 14/002,782.
Official Action dated Apr. 20, 2015 From the US Patent and Trademark Office Re. U.S. Appl. No. 14/002,782.
Restriction Official Action dated Jan. 13, 2015 From the US Patent and Trademark Office Re. U.S. Appl. No. 14/002,782.
Dadon-Nachum et al. "Therapeutic Effect of Myogenic Cells Modified to Express Neurotrophic Factors in A Rat Model of Sciatic Nerve Injury", Journal of Stem Cells and Regenerative Medicine, XP055030565, 8 (1): 21-27, Apr. 14, 2012.
Mohajeri et al. "Intramuscular Grafts of Myoblasts Genetically Modified to Secrete Glial Cell Line-Derived NeutrotrophicFactor Prevent Motoneuron Loss and Disease Progression in A Mouse Model of Familial Amyotrophic Lateral Sclerosis", Human Gene Therapy, XP002183001, 10(11): 1853-1866, Jul. 20, 1999.

(Continued)

*Primary Examiner* — Valarie E Bertoglio
(74) *Attorney, Agent, or Firm* — Browdy and Neimark, PLLC

(57) ABSTRACT

An isolated muscle progenitor cell being MyoD positive, CD34 negative and CD45 negative is disclosed. The muscle progenitor cell is genetically modified to express at least one neurotrophic factor. In addition, cell populations are disclosed, comprising at least four subpopulations of muscle cells each being genetically modified to express a different neurotrophic factor, wherein said neurotrophic factor is selected from the group consisting of glial derived neurotrophic factor (GDNF), insulin growth factor (IGF-1), vascular endothelial growth factor (VEGF) and brain-derived neurotrophic factor (BDNF). Uses of the cell populations are also disclosed.

**4 Claims, 11 Drawing Sheets
(11 of 11 Drawing Sheet(s) Filed in Color)
Specification includes a Sequence Listing.**

(56) References Cited

OTHER PUBLICATIONS

Myckatyn et al. "Muscle-Derived GDNF Facilitates Motor Nerve Recovery Following Sciatic Nerve Crush Injury", Journal of the American College of Surgeons, 205: S92, 2007.
Park et al. "Growth Factor-Expressing Hurnan Neural Progenitor Cell Grafts Protect Motor Neurons But Do Not Ameliorate Motor Performance and Survival in ALS Mice", Experimental and Molecular Medicine, XP055030512, 41 (7): 487-500, Jul. 31, 2009.
Saccon et al. Is SOD1 Loss of Fnnction Involved in Amyotrophic Lateral Sclerosis?, Brain, 2013: 1-7, Advance Access Published May 17, 2013.
Sarig et al. "Regeration and Transdifferentiation Potential of Muscle-Derived Stem Cells Propagated as Myospheres", Stem Cells, 24: 1769-1778, 2006.
Suzuki et al. "Combining Growth Factor and Stem Cell Therapy for Amyotrophic Lateral Sclerosis", Trends in Neurosciences, XP022576525, 31(4): 192-198, Apr. 2008.
Sarig et al., (Stem Cells 2006; 24: 1769-1778).
Leronimakis (Jun. 2010, PLoS One, 5:e10920, pp. 1-16.

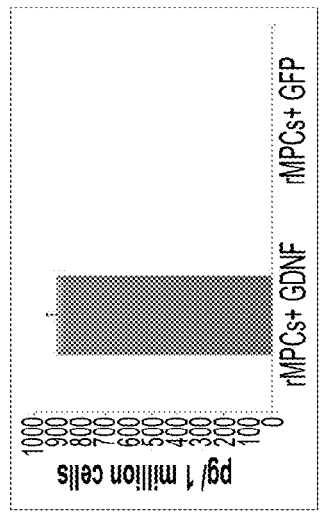
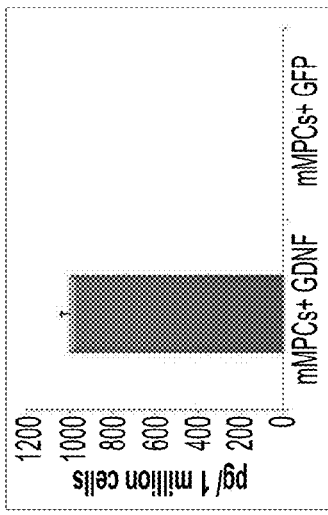
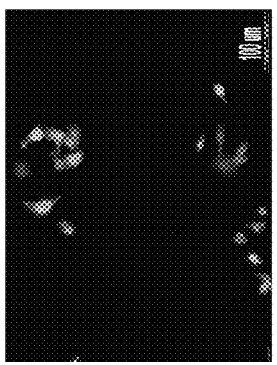
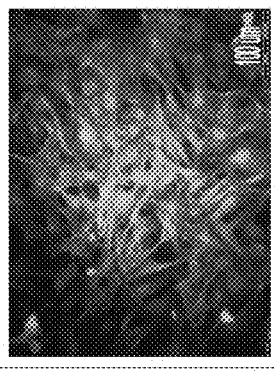
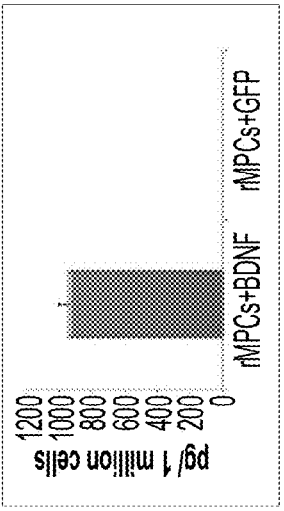
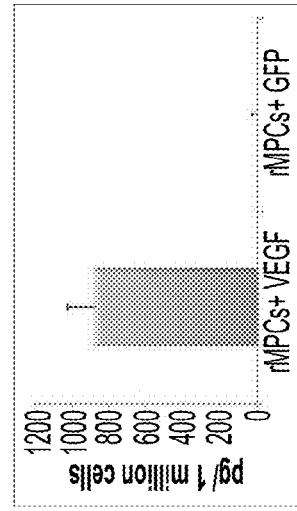
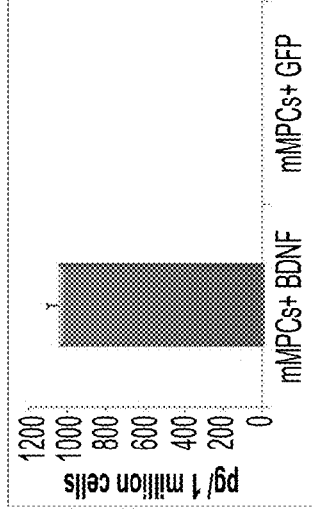
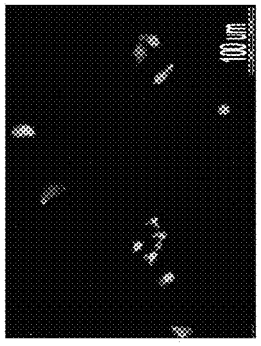
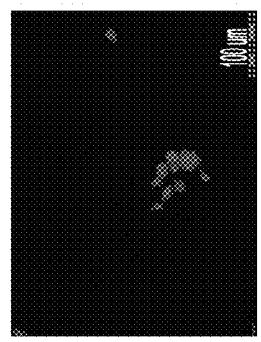
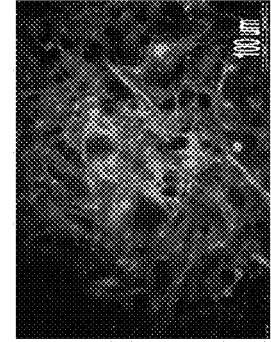

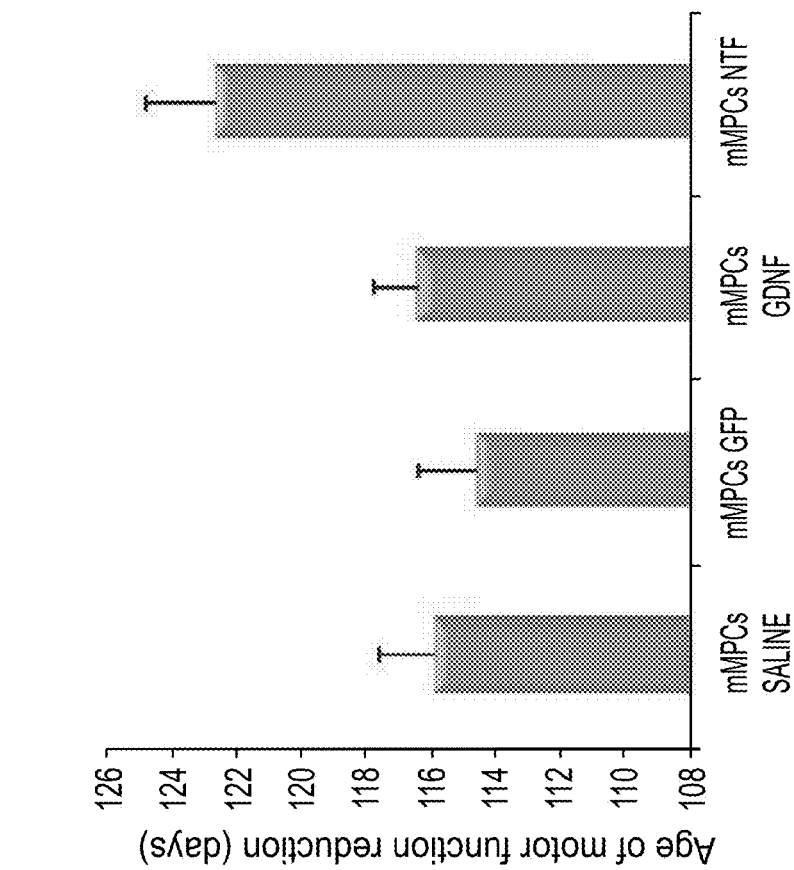
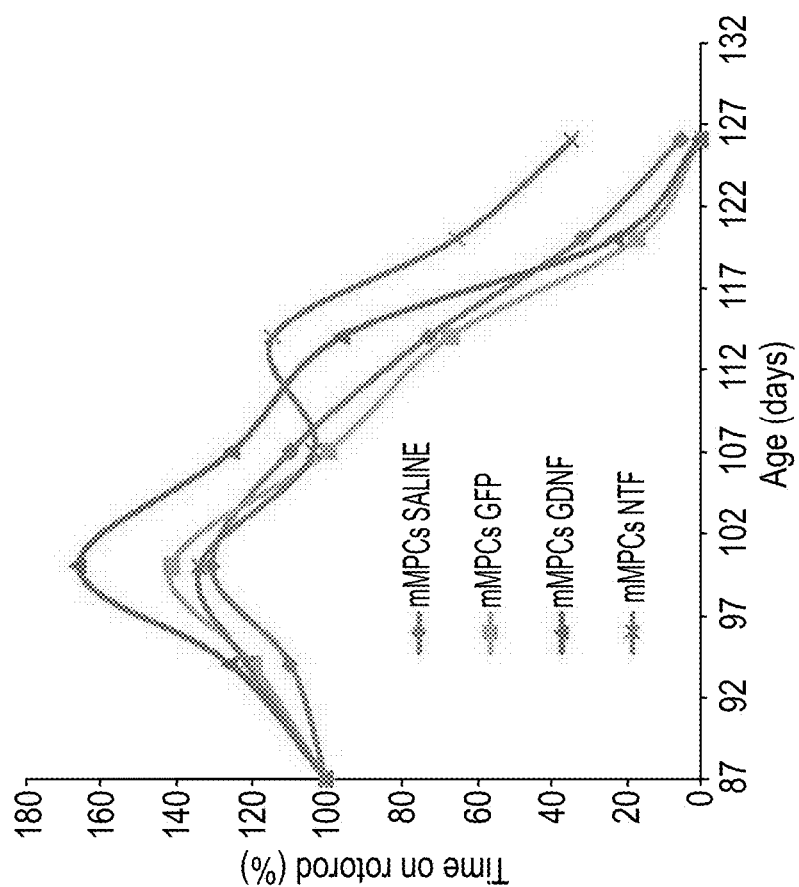
FIG. 7B
FIG. 7A

GENETICALLY MODIFIED MUSCLE CELLS WHICH EXPRESS NEUROTROPHIC FACTORS

RELATED APPLICATIONS

This application is a continuation of U.S. patent application Ser. No. 15/180,152 filed on Jun. 13, 2016, now abandoned, which is a division of U.S. patent application Ser. No. 14/002,782, filed on Sep. 3, 2013, now U.S. Pat. No. 9,365,828, which was a National Phase of PCT Patent Application No. PCT/IB2012/050976 having International Filing Date of Mar. 1, 2012, which claims the benefit of priority under 35 USC 119(e) of U.S. Provisional Patent Application No. 61/448,712 filed on Mar. 3, 2011. The contents of the above applications are all incorporated by reference as if fully set forth herein in their entirety.

SEQUENCE LISTING STATEMENT

The Sequence Listing in ASCII text file format of 47,935 bytes in size, created on Mar. 14, 2019, with the file name "2019 Mar. 14SequenceListing-OFFEN3B," filed in the U.S. Patent and Trademark Office on even date herewith, is hereby incorporated herein by reference.

FIELD AND BACKGROUND OF THE INVENTION

The present invention, in some embodiments thereof relates to genetically modified muscle cells for the treatment of neurodegenerative disorders.

Amyotrophic lateral sclerosis (ALS), also known as Lou Gehrig's disease, was first described in 1869 by a French neurologist, Jean Martin Charcot. This is a progressive, lethal disease that leads to degeneration of upper and lower motor neurons. Death of the upper motor neurons found in the motor cortex in the brain, leads to spasticity, hyperexcitability of reflexes and the appearance of pathological reflexes. The death of the lower motor neurons, which is found in the brain stem and in the spinal cord, leads to weakness and atrophy of the muscles followed by progressive paralysis.

ALS has a worldwide prevalence of 1-2 per 100,000, and mortality is caused within 3-5 years of the onset of the disease due to respiratory failure. ALS occurs mainly in adults (45-60 of age), and most cases are sporadic, although 5 to 10% of ALS cases are inherited in an autosomal dominant pattern of which about 20% are caused by a mutation in the Cu/Zn superoxide dismutase (SOD1) gene on chromosome 21. The disease results from the overactivity of the SOD1 gene and not from the damage in its antioxidant activity. The etiology of sporadic ALS is unknown, although it is generally believed that sporadic and familial ALS may share pathological mechanisms.

The pathophysiology of the disease includes a reduced secretion of neurotrophic factors (NTFs), protein aggregations, malfunctioning of the mitochondria, rupture in the axonal passage, destruction in the calcium metabolism, changes in the skeletal proteins, high levels of glutamate and oxidative damage. Preventing or slowing motor neurons degeneration and death in ALS are critical goals of future therapies, as are means of enhancing axonal regeneration.

Several studies concerning peripheral nerve pathology have demonstrated that neurotrophic factors play an important role in the development, maintenance and regeneration of the nervous system. The brain derived neurotrophic factor (BDNF) was shown to prevent the loss of motor units and to contribute to the maintenance of muscle mass when administered to the hind limb muscles of mice after peripheral nerve injury. The glial derived neurotrophic factor (GDNF) and the insulin growth factor 1 (IGF-1) are two of the most potent survival factors known for peripheral neurons. Several studies have shown that both GDNF and IGF-1 can prevent neuronal degeneration in mice and rats after axotomy, as well as the programmed cell death of motor neurons during development [3, 6-9]. In the SOD1$^{G93A}$ transgenic mice model for amyotrophic lateral sclerosis (ALS), overexpression of GDNF and/or IGF-1 in muscles, resulted in hyperinnervation of the muscles by motor neurons [3, 6-13]. Moreover, GDNF is important for neuron branching at the NMJ and for modulating synaptic plasticity [14]. Increased expression of GDNF in the muscles of SOD1$^{G93A}$ transgenic mice delays disease onset, improves locomotor performance, and increases their lifespan. In addition, the survival of motor neurons is increased when GDNF levels in the muscles of SOD1$^{G93A}$ transgenic mice are high. The vascular endothelial growth factor (VEGF) is another factor contributing to the pathogenesis of ALS and the increased expression of VEGF in motor neuron of SOD1$^{G93A}$ transgenic mice, augmented their survival and enhanced motor performance [15-16]. Moreover, intracerebroventricular administration of VEGF in a rat model of ALS, dramatically increased motor neuron survival and an intraperitoneal injection of VEGF led to the preservation of NMJs [17-18]. Unfortunately, clinical trials of systemic or intrathecal administration of growth factors to ALS patients have not been effective, probably due in part to their short half-life, low concentrations at target sites, and high incidence of side effects [10-11].

Sarig et al., [Stem Cells 2006; 24: 1769-1778] teaches isolated populations of muscle progenitor cells (MPCs).

Mohajeri et al [Human Gene Therapy, 10:1853-1866 (Jul. 20, 1999) teaches the use of primary myoblast cells genetically modified to express GDNF for the treatment of motor neuron diseases.

U.S. Patent Application No. 20050238625 teaches the use of skeletal muscle cells genetically modified to express neurotrophic factors for the treatment of nerve diseases.

U.S. Patent Application No. 20030161814 teaches the use of skeletal muscle cells genetically modified to express GDNF for the treatment of motor neuron diseases.

SUMMARY OF THE INVENTION

According to an aspect of some embodiments of the present invention there is provided an isolated cell population, comprising at least four subpopulations of muscle cells, each of the at least four subpopulation being distinct in that they are genetically modified to express a different neurotrophic factor, wherein the neurotrophic factor is selected from the group consisting of glial derived neurotrophic factor (GDNF), insulin growth factor (IGF-1), vascular endothelial growth factor (VEGF) and brain-derived neurotrophic factor (BDNF).

According to an aspect of some embodiments of the present invention there is provided an isolated muscle progenitor cell being MyoD positive, CD34 negative and CD45 negative, genetically modified to express at least one neurotrophic factor.

According to an aspect of some embodiments of the present invention there is provided a method of treating a nerve disease or damage, comprising administering to a subject in need thereof a therapeutically effective amount of the isolated cell population described herein, thereby treating the nerve disease or damage.

According to an aspect of some embodiments of the present invention there is provided a method of treating a nerve disease or disorder in a subject, comprising introducing into the muscle cells of the subject a first polynucleotide which encodes a first neurotrophic factor, a second polynucleotide which encodes a second neurotrophic factor and a third polynucleotide which encodes a third neurotrophic factor, each of the first, the second and the third neurotrophic factor being mutually distinct, thereby treating the nerve disease or disorder.

According to an aspect of some embodiments of the present invention there is provided a method of treating a nerve disease or damage, comprising administering to a subject in need thereof a therapeutically effective amount of an isolated population of muscle progenitor cells, the muscle progenitor cells being MyoD positive, CD34 negative and CD45 negative, genetically modified to express at least one neurotrophic factor, thereby treating the nerve disease or damage.

According to some embodiments of the invention, the muscle cells comprise progenitor cells.

According to some embodiments of the invention, the muscle progenitor cells comprise skeletal muscle progenitor cells.

According to some embodiments of the invention, each of the at least four subpopulations are present in substantially equal amounts.

According to some embodiments of the invention, each of the at least four subpopulations are present in alternate ratios.

According to some embodiments of the invention, each of the at least four subpopulations is genetically modified to express a single neurotrophic factor.

According to some embodiments of the invention, the isolated muscle progenitor cell is isolated by at least two rounds of differential plating, wherein a first round of the differential plating is effected on plastic plates and a second round of the differential plating is effected on a plate coated with a substance selected from the group consisting of collagen, gelatin and poly-lysine.

According to some embodiments of the invention, the at least one neurotrophic factor is selected from the group consisting of glial derived neurotrophic factor (GDNF), nerve growth factor (NGF), vascular endothelial growth factor (VEGF), brain-derived neurotrophic factor (BDNF), neurotrophin-3 (NT-3), neurotrophin-4/5, Neurturin (NTN), Persephin, brain derived neurotrophic factor (BDNF), artemin (ART), ciliary neurotrophic factor (CNTF), insulin growth factor-I (IGF-1) and Neublastin.

According to some embodiments of the invention, the neurotrophic factor is selected from the group consisting of glial derived neurotrophic factor (GDNF), vascular endothelial growth factor (VEGF), brain-derived neurotrophic factor (BDNF) and insulin growth factor-I (IGF-1).

According to some embodiments of the invention, the isolated muscle progenitor cell is an adult, muscle progenitor cell.

According to some embodiments of the invention, the isolated muscle progenitor cell is a skeletal muscle progenitor cell.

According to some embodiments of the invention, the isolated muscle progenitor cell expresses at least two of the GDNF, VEGF, BDNF and IGF-1.

According to some embodiments of the invention, the isolated muscle progenitor cell expresses each of the GDNF, VEGF, BDNF and IGF-1.

According to some embodiments of the invention, the method further comprises introducing into the muscle cells of the subject a fourth polynucleotide which encodes a fourth neurotrophic factor, each of the first, the second, the third and the fourth neurotrophic factor being mutually distinct.

According to some embodiments of the invention, the first neurotrophic factor is GDNF, the second neurotrophic factor is VEGF, the third neurotrophic factor is BDNF and the fourth neurotrophic factor is IGF-1.

According to some embodiments of the invention, the method is effected in vivo.

According to some embodiments of the invention, the method is effected ex vivo.

According to some embodiments of the invention, the administering is effected by transplanting the isolated population of muscle cells into the muscle of the subject.

According to some embodiments of the invention, the first polynucleotide, the second polynucleotide and the third polynucleotide are comprised in a single nucleic acid construct.

According to some embodiments of the invention, the first polynucleotide, the second polynucleotide and the third polynucleotide are each comprised in a different nucleic acid construct.

According to some embodiments of the invention, the isolated population of muscle cells are for use in the treatment of a nerve disease or damage.

According to some embodiments of the invention, the nerve disease is a neuromuscular disease.

According to some embodiments of the invention, the nerve disease is a motor neuron disease.

According to some embodiments of the invention, the nerve damage is selected from the group consisting of peripheral nerve injury, peripheral nerve inflammation, autonomic nerve injury, pelvic nerve damage, burn, blunt trauma, back injury, back pain and sciatica.

According to some embodiments of the invention, the neuromuscular disease is selected from the group consisting of a spinal muscular atrophy, a amyotrophic lateral sclerosis (ALS), a Werdnig Hoffman disease, a Charcot-Marie tooth disease, multiple sclerosis, myasthenia gravis, muscular dystrophy and a myositis.

According to some embodiments of the invention, the motor neuron disease is selected from the group consisting of amyotrophic lateral sclerosis, primary lateral sclerosis (PLS), pseudobulbar palsy and progressive bulbar palsy.

According to some embodiments of the invention, the cells are autologous cells.

According to some embodiments of the invention, the cells are non-autologous cells.

According to some embodiments of the invention, the neuromuscular disorder is ALS.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-1K are graphs and photographs illustrating that rat and mouse muscle progenitor cells (MPCs) express and secrete neurotrophic factors. MPCs transfected with the neurotrophic genes BDNF (rat: A-B, mouse: H-I); GDNF (rat: C-D, mouse: J-K); VEGF (rat: E-F) and IGF-1 (rat: G) as measured by immunohistochemistry and ELISA.

Figure 2B:
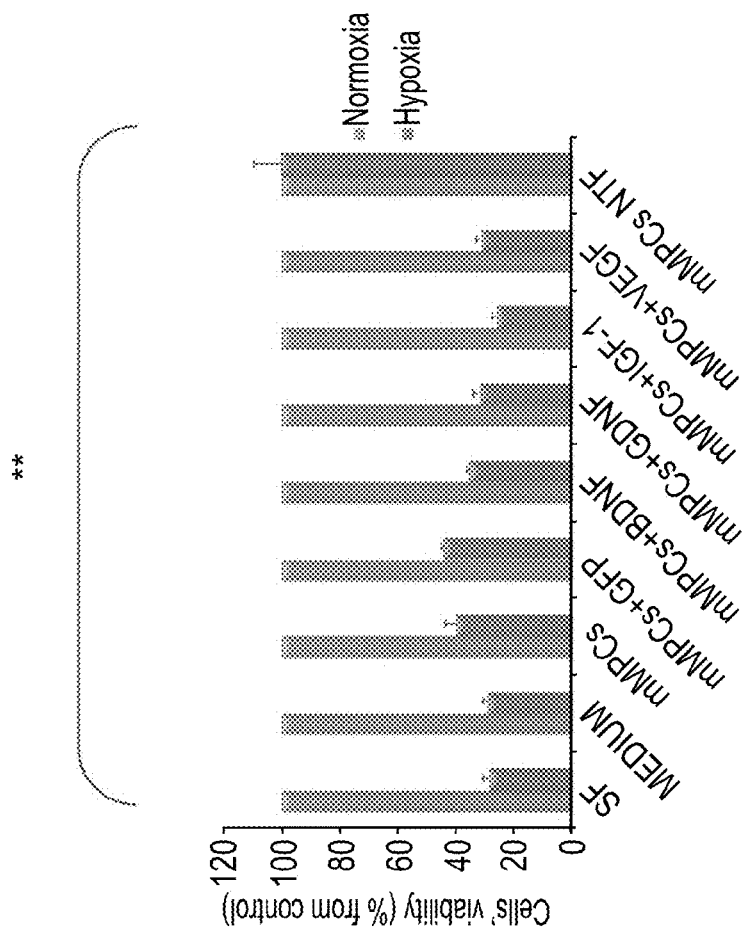
Figure 2A:
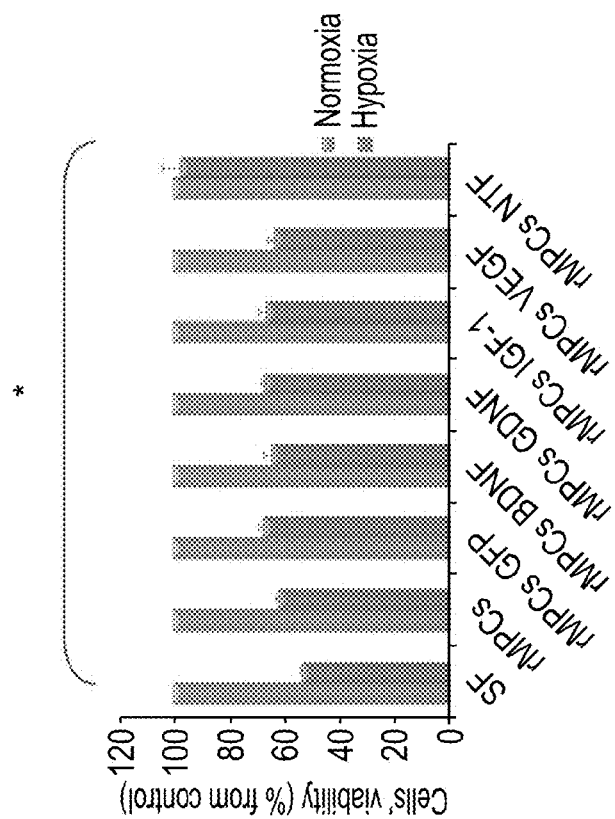
Figure 2C:
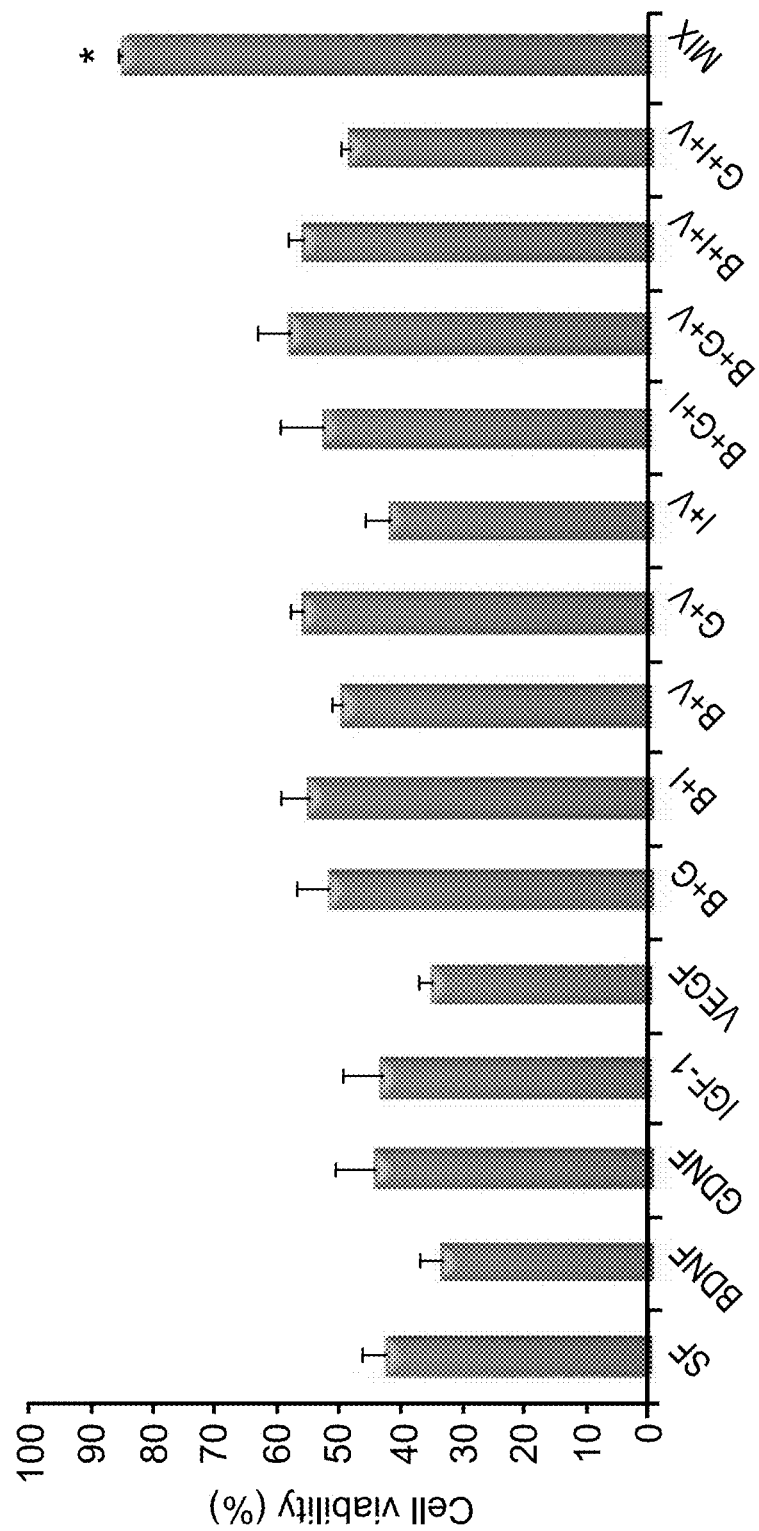

FIGS. 2A-2C illustrate MPCs-mix (also referred to herein as MPCs-NTF) conditioned media protects motor neuron cell line (NSC-34) in culture against hypoxic stress. After 48 hours in hypoxic environment, the combination of the cells' conditioned media protects NSC34 cells viability (rat MPCs-mix;A; mouse MPCs-mix: B, C. $*p<0.05$, $**p<0.01$).

Figure 3:
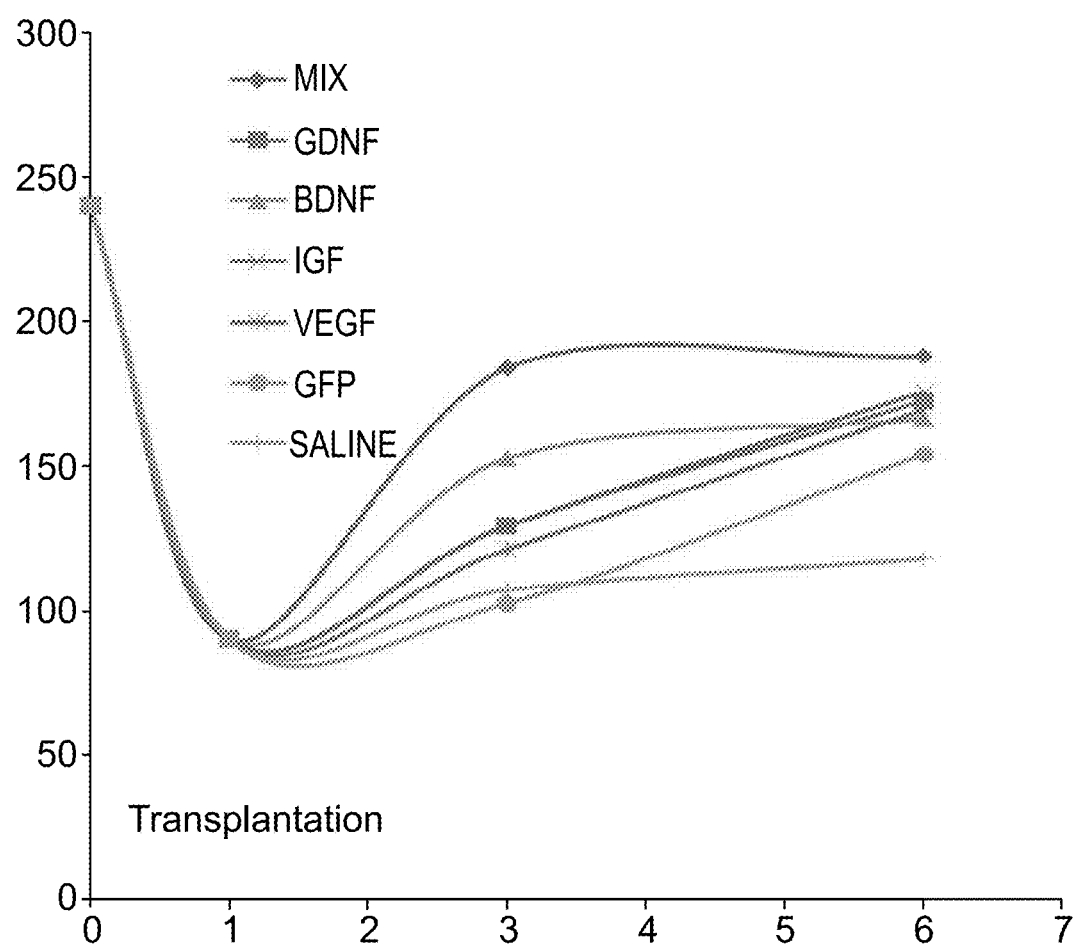

FIG. 3 illustrates that rat MPCs-mix cells inoculation after sciatic nerve injury in rats, rescue the motor functioning. One day after mechanical crush of the right hind limb, rat MPCs expressing each one of the four NTFs, combination of—NTF, GFP or PBS were inoculated into the injury site. Motor recovery was examined by rotorod test and presented by time spent on rod. In rats injected with combined MPCs-mix, motor function measured by rotorod was markedly preserved comparing to the other treatment and control groups. (n=9, $*p<0.05$ as determined by ANOVA test).

Figure 4:
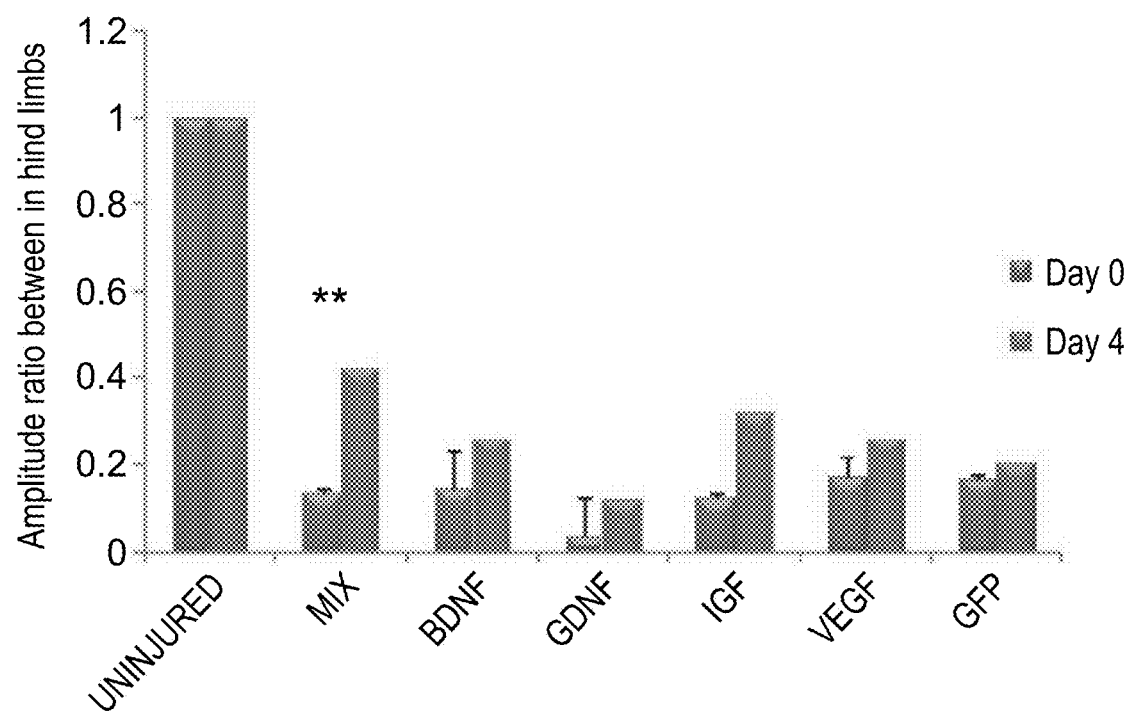

FIG. 4 is a bar graph illustrating restoration of nerve conduction following rat MPCs-mix inoculation. Four days following rat MPCs expressing one of the four NTFs, combination of MPCs-mix, MPCs-GFP or PBS transplantation into sciatic nerve crush site, nerve conduction was tested by electromyography. Compound muscle action potential presented as a ratio between the injured and uninjured hind limbs (n=3, means±SEM, $**p<0.01$ as determined by student t-test).

Figure 5A:
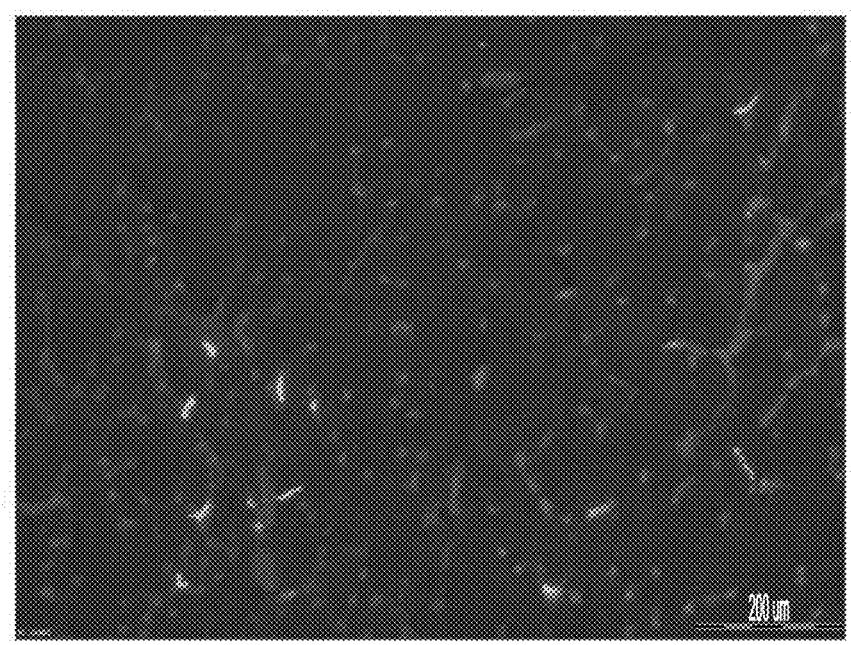
Figure 5B:
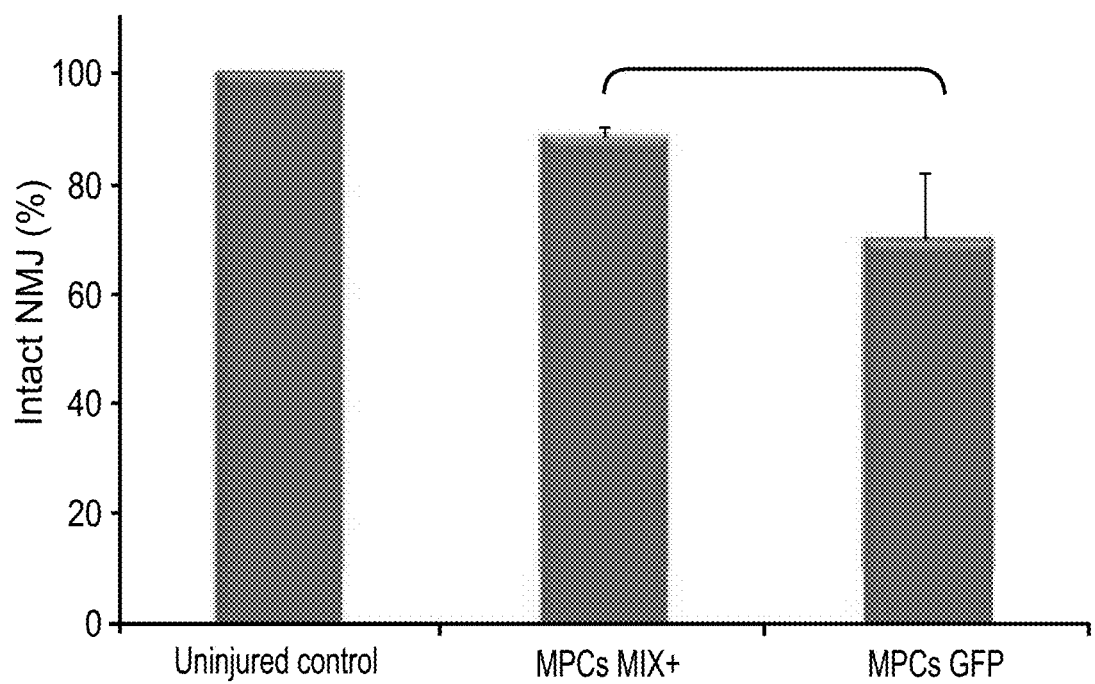
Figure 6B:
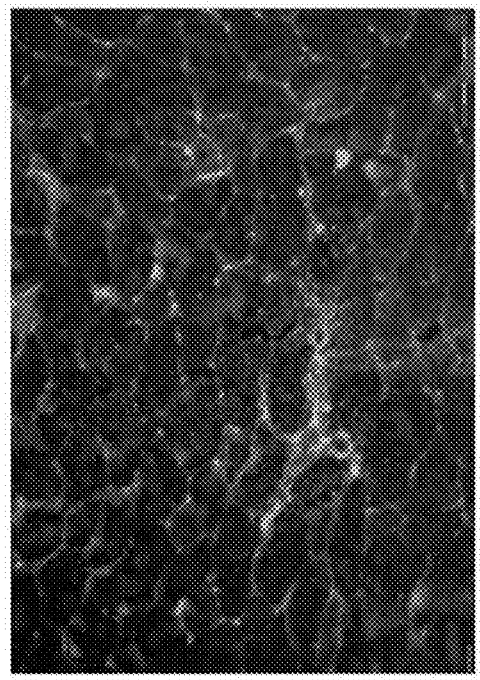
Figure 6D:
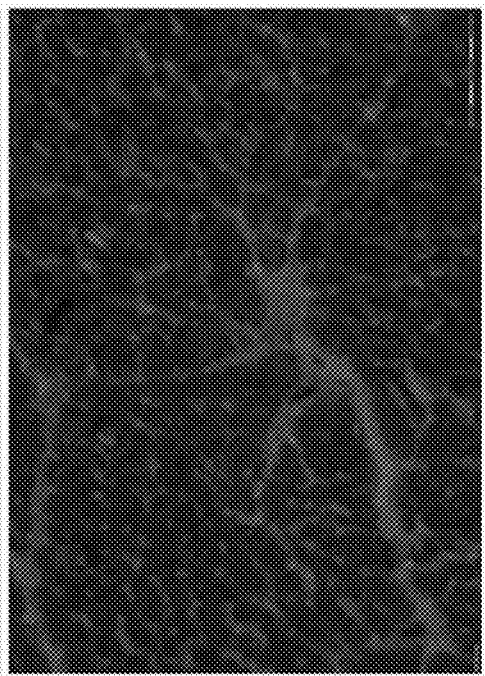
Figure 6A:
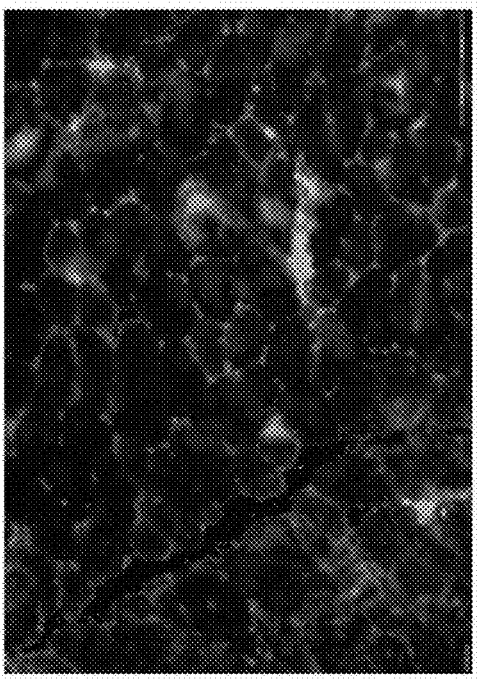
Figure 6C:
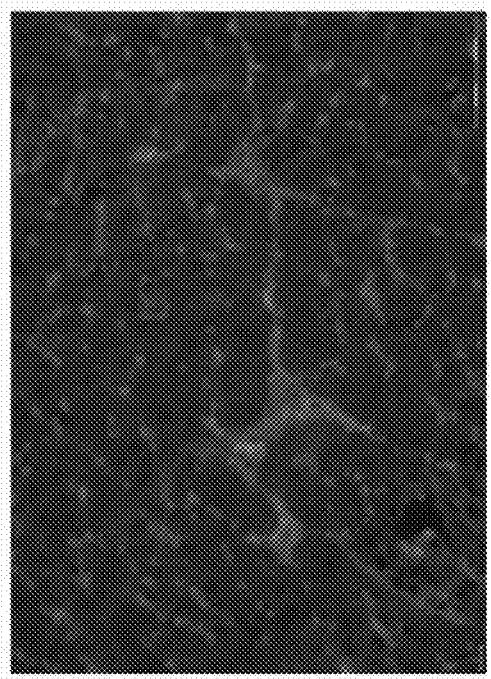

FIGS. 5A-5B illustrate that RMPCs NTF transplantation preserves innervated neuromuscular junctions. Two weeks following sciatic nerve crush and transplantation of combination rat MPCs-mix or MPCs-GFP rats were sacrificed. Hind limbs muscles were double stained using alpha bungarotoxin (green) and anti-synaptophysin antibodies (red). Representative image of hind limb muscle section transplanted with rat MPCs-mix (A). Quantification of integrated NMJs (B) (n=5, means+SEM, $*p<0.05$, determined by student t-test).

FIGS. 6A-6D are photographs illustrating that rat MPCs-mix expressing neurotrophic factors in transplanted muscles. Two weeks following sciatic nerve crush and transplantation of rat MPCs-mix, rats were sacrificed. Hind limb muscles sections were stained with antibodies against BDNF (A); GDNF (B); IGF-1 (C) and VEGF (D).

FIGS. 7A-7B illustrate that mouse MPCs-mix cells transplantation into SOD1 transgenic mice significantly delay symptoms onset. At 87 days, no significant difference was observed among experimental groups. Over the next 40 days, performance of mice deteriorated significantly, whereas the performance of MPCs-mix treated mice show a significant better motor function as indicated by the balancing ability on the rotorod (A). Mice treated with MPCs-mix demonstrate 50% reduction in motor activity eight days after mice treated with saline/Data shown for female mice (B). Male mice data are not shown ($p<0.05$, n=12).

Figure 8A:
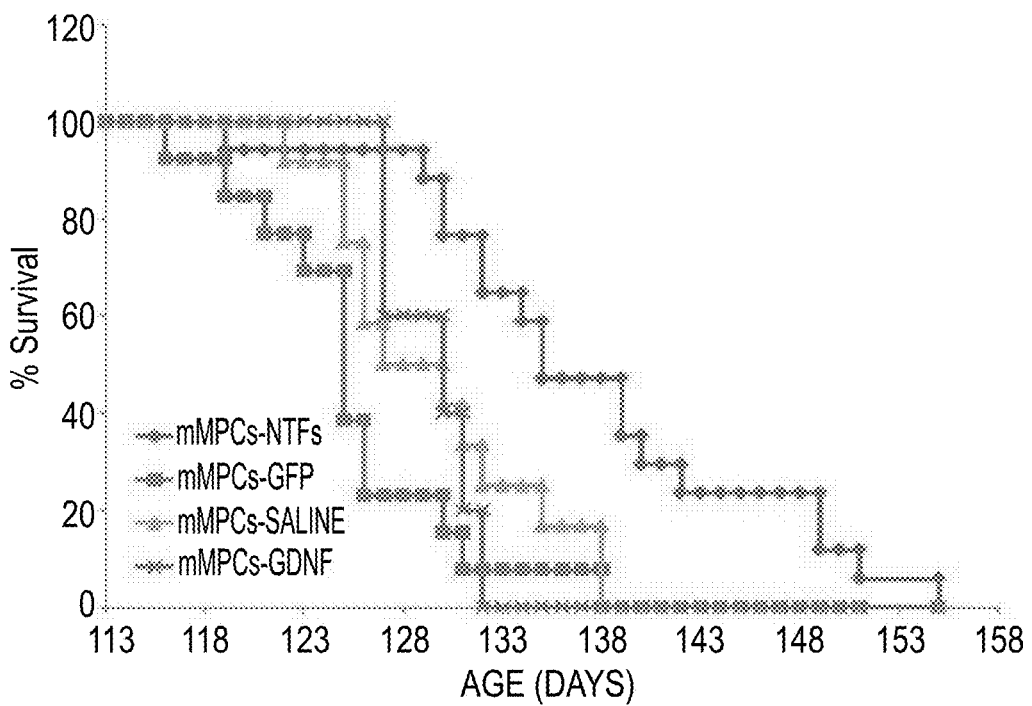
Figure 8B:
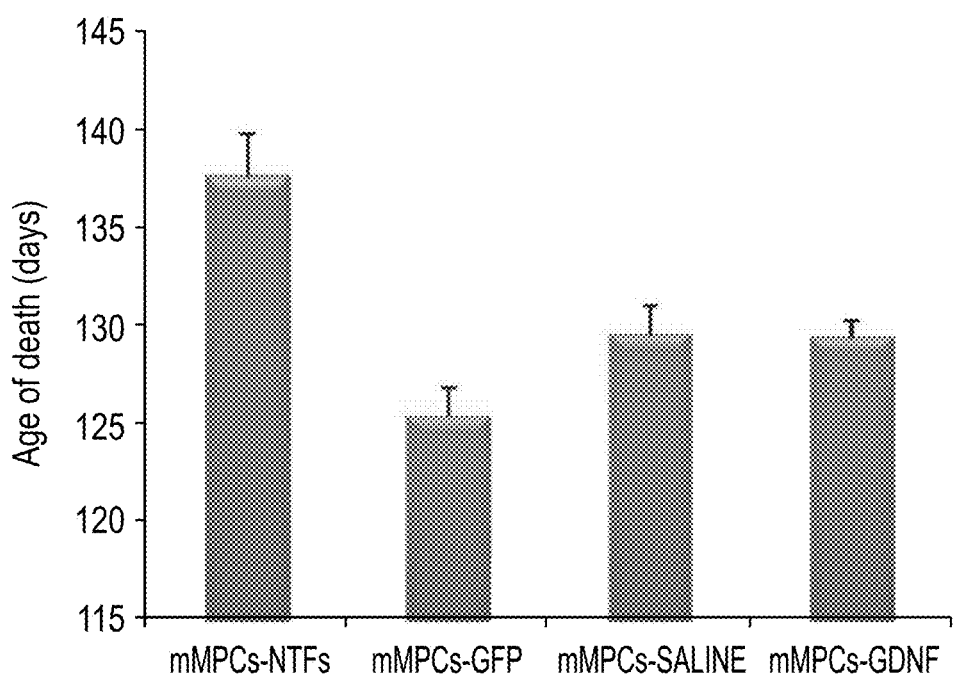

FIGS. 8A-8B illustrate that MPCs-mix transplantation extend the survival of SOD1 transgenic mice. Comparison of survival of SOD1 transgenic mice treated with saline/MPCs-GFP/MPCs-GDNF or MPC-mix. (A) Kaplan-Meier graph demonstrates that the cumulative survival of MPCs-mix treated SOD1 mice (n=17) is prolonged compared with saline (n=12)/MPCs-GFP (n=12) or MPCs-GDNF treaded SOD1mice (n=12). (B) There is a significant prolongation of the average life span by 10-13 days in the MPCs-mix treated group compared with the three other groups ($*p<0.05$).

Figure 9A:
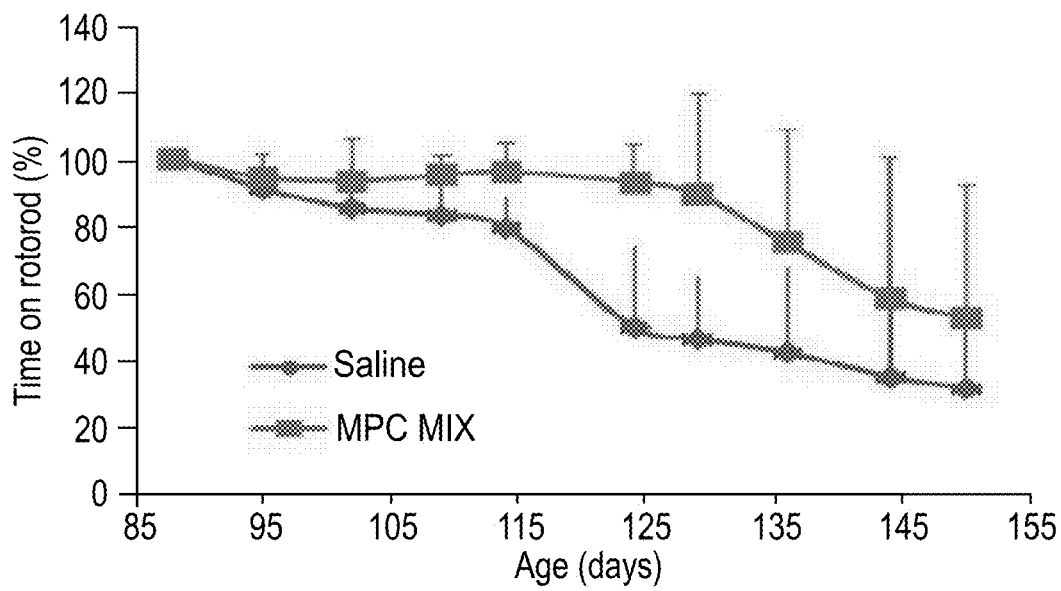
Figure 9B:
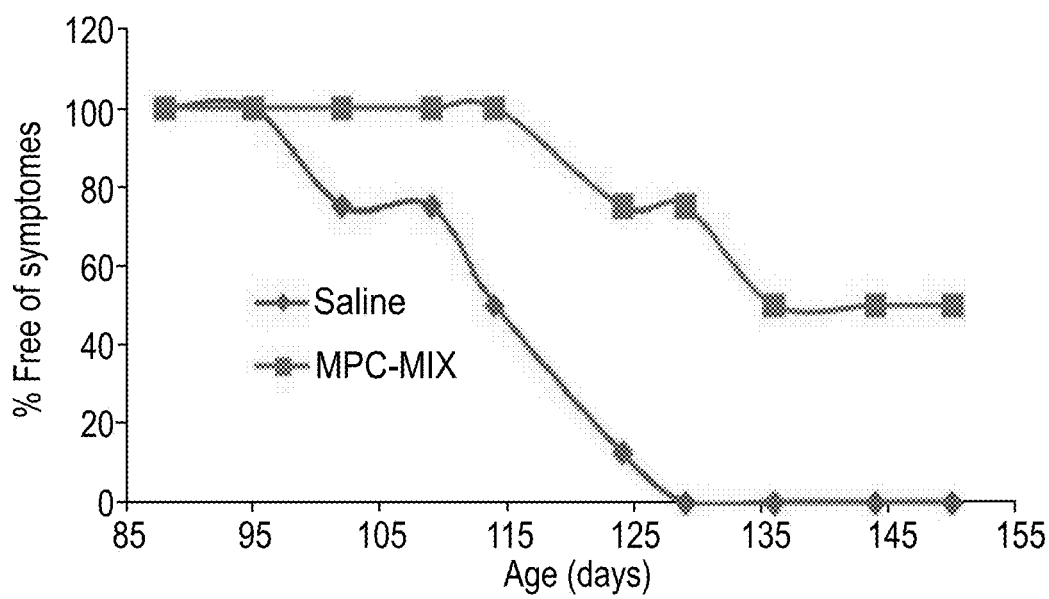

FIGS. 9A-9B are graphs illustrating that the transplantation of mouse MPC-mix delayed the onset of symptoms in SOD1 mice. Mouse MPC-mix were injected on day 90, 104, 118 age into SOD1 mice (n=8, C57b1 background). (A) Rotarod performance ($P<0.01$ as determined by repeated measurements). (B) The percent of mice that are free of symptoms (20% reduction on rotarod).

Figure 10:
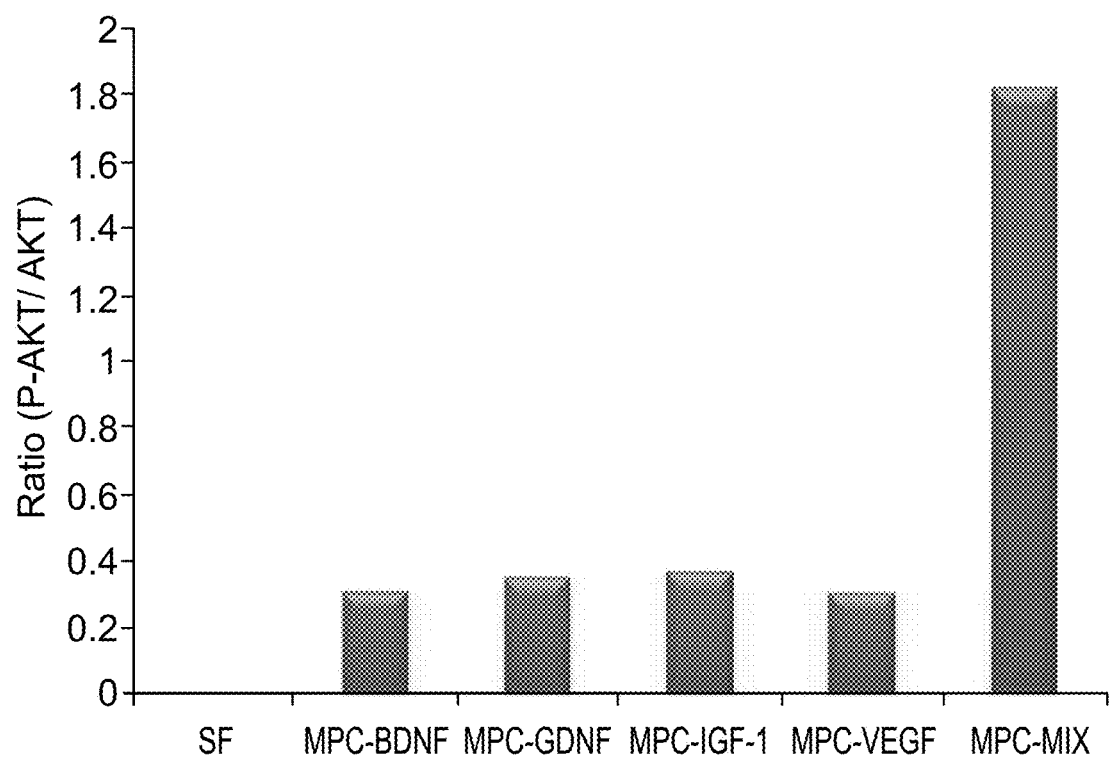

FIG. 10 is a bar graph illustrating that MPC-mix conditioned media synergistically increases akt phosphorylation in motor neuron cell line under hypoxic conditions. Conditioned media from various MPC clones were added to NSC-34 cells for 24 hours in hypoxic environment. The ratio of AKT vs. phosphorylated-AKT proteins was analyzed on Western blot using specific antibody.

DESCRIPTION OF SPECIFIC EMBODIMENTS OF THE INVENTION

The present invention, in some embodiments thereof, relates to muscle cells which have been genetically modified to express neurotrophic factors (NTFs) and uses thereof.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors uncovered that simultaneously up-regulating four neurotrophic factors in muscle cells had a synergistically greater therapeutic effect when compared with the up-regulation of one neurotrophic factor as tested in mouse models for motor neuron pathologies.

The present inventors propose the generation of muscle cells populations comprising 4 subpopulations, each being genetically modified to express a different neurotrophic factor. By mixing the different sub-populations in alternate ratios, the present inventors propose the generation of cell populations tailored for the treatment of particular nerve and/or muscle disorders.

As well as genetic modification of the polynucleated muscle fibers themselves, the present inventors propose the genetic modification of mononucleated muscle precursors for this purpose. For example, a very slow adherent cell population of adult skeletal muscle cells has previously been isolated Sarig et at, [Stem Cells 2006; 24: 1769-1778], which could be propagated in suspension as unattached clusters, consisting of pure populations of muscle progenitor cells (MPCs). These cells were shown be MyoD positive and CD34 and CD45 negative. Using these cells, the present inventors produced genetically manipulated muscle progenitor cells (MPCs) as a vehicle to facilitate expression of the genes encoding neurotrophic factors (NTFs); BDNF, GDNF, IGF-1 and VEGF via the generation of 4 distinct subpopulations.

These genetically manipulated MPCs (referred to herein as MPCs-NTFs or MPC-mix) were shown to be useful for the treatment of motor neuron pathology in two animal models. In the rat model of sciatic nerve crush, the animals showed improved motorod performance (FIG. 3), an improved compound muscle action potential (CMAP; FIG. 4) and increased preservation of the innervated neuromuscular junction (NMJ; FIGS. 5A-B)) following transplantation of the genetically modified MPCs as compared to control animals. In SOD1$^G$ mice, a model for ALS, the animals showed a delay in reduction of motor function (FIGS. 7A-B and 9A-B) and a prolonged lifespan (FIGS. 8A-B).

Thus, according to one aspect of the present invention, there is provided an isolated muscle progenitor cell genetically modified to express at least one neurotrophic factor.

The muscle progenitor cells of this aspect of the present invention may express myogenic proteins including, but not limited to the intermediate filament protein desmin, MyoD, Myf-5 and Pax-7.

According to a particular embodiment, the muscle progenitor cells are MyoD positive, CD34 negative and CD45 negative.

Ex vivo and in vitro cell populations useful as a source of cells may include fresh or frozen cell populations obtained from embryonic, fetal, pediatric or adult tissue. The progenitor cells may be obtained from any mammalian species, e.g. human, equine, bovine, porcine, canine, feline, rodent, e.g. mice, rats, hamster, primate, etc.

According to a particular embodiment, the muscle progenitor cells are derived from adult tissue.

Methods of obtaining skeletal muscle progenitor cells are known in the art—see for example Sarig et al [Stem Cells 2006; 24: 1769-1778], the contents of which are incorporated herein by reference.

Primary skeletal muscles cells may be obtained from subjects during a biopsy or surgical procedure. The biopsy can be obtained by using a biopsy needle under a local anesthetic, which makes the procedure quick and simple. The small biopsy core of the isolated tissue can then be expanded and cultured to obtain the tissue cells.

Methods for the isolation and culture of cells are discussed by Freshney, Culture of Animal Cells. A Manual of Basic Technique, 2d Ed., A. R. Liss, Inc., New York, 1987, Ch. 9, pp. 107-126. Cells may be isolated using techniques known to those skilled in the art. For example, the tissue can be cut into pieces, disaggregated mechanically and/or treated with digestive enzymes and/or chelating agents that weaken the connections between neighboring cells making it possible to disperse the tissue into a suspension of individual cells without appreciable cell breakage. If necessary, enzymatic dissociation can be accomplished by mincing the tissue and treating the minced tissue with any of a number of digestive enzymes either alone or in combination. These include but are not limited to trypsin, chymotrypsin, collagenase, elastase, and/or hyaluronidase, DNase, pronase, and dispase. Mechanical disruption can also be accomplished by a number of methods including, but not limited to, scraping the surface of the tissue, the use of grinders, blenders, sieves, homogenizers, pressure cells, or insonators to name but a few.

The cells are then suspended in a proliferation medium. Typically, such a medium may comprise an antibiotic and additional components which aid in the proliferation of the muscle progenitor cells—such factors may include for example fetal calf serum, steroids, basic fibroblast growth factor, insulin and glutamine.

According to one embodiment, the heterogeneous cell population obtained from tiypsinized skeletal muscle is pre-plated in untreated (e.g. plastic) cell culture plates. After the adherence of the "fibroblastic" cells, the unattached cells are collected and plated in gelatin/poly-lysine/collagen-coated plates to enable the adherence of the majority of muscle progenitor cells.

According to one embodiment, after at least one day, the non-adherent cells of the gelatin culture are collected and maintained by serial passages either as suspended myospheres or as adherent cultures. This results in a population of cells comprising muscle progenitor cells which are MyoD positive, CD34 negative and CD45 negative.

Cells which are CD34 negative and CD45 negative may be selected using various methods known in the art including fluorescent activated cell sorting (FACS). Alternatively or in addition, magnetic cell sorting (MACS) or immunopanning may be employed to sort the cells.

The above described cell populations are genetically modified to express at least one neurotrophic factor.

As used herein, the phrase "neurotrophic factor" refers to a cell factor that acts on the cerebral nervous system comprising growth, differentiation, functional maintenance and/or survival effects on neurons.

Examples of neurotrophic factors include, but are not limited to, glial derived neurotrophic factor (GDNF), GenBank accession Nos. L19063/L15306 (SEQ ID NO: 1) and AAA67910 (SEQ ID NO: 2); nerve growth factor (NGF), GenBank accession Nos. X53655 (SEQ ID NO: 3) CAA37703 (SEQ ID NO: 4); brain-derived neurotrophic factor (BDNF), GenBank accession Nos. X91251 (SEQ ID NO: 5) and CAA62632 (SEQ ID NO: 6); neurotrophin-3 (NT-3), GenBank Accession Nos. M37763 (SEQ ID NO: 7) and AAA59953 (SEQ ID NO: 8); neurotrophin-4/5; Neurturin (NTN), GenBank Accession Nos. NM_004558 (SEQ ID NO: 9) and NP_004549 (SEQ ID NO: 10); Neurotrophin-4, GenBank Accession Nos. M86528 (SEQ ID NO: 11) and AAA60154 (SEQ ID NO: 12); Persephin, GenBank accession Nos. AF040962 (SEQ ID NO: 13) and AAC39640 (SEQ ID NO: 14); artemin (ART), GenBank accession Nos. AF115765 (SEQ ID NO: 15) and AAD13110 (SEQ ID NO: 16); ciliary neurotrophic factor (CNTF), GenBank accession Nos. NM_000614 (SEQ ID NO: 17) and NP_000605 (SEQ ID NO: 18); insulin growth factor-I (IGF-1), GenBank accession Nos. NM_000618 (SEQ ID NO: 19) and NP_000609 (SEQ ID NO: 20); and Neublastin GenBank accession Nos. AF120274 (SEQ ID NO: 21) and AAD21075 (SEQ ID NO: 22).

A neurotrophic factor of the present invention also refers to homologs (e.g., polypeptides which are at least 50%, at least 55%, at least 60%, at least 65%, at least 70%, at least 75%, at least 80%, at least 85%, at least 87%, at least 89%, at least 91%, at least 93%, at least 95% or more say 100% homologous to the above mentioned sequences as determined using BlastP software of the National Center of Biotechnology Information (NCBI) using default parameters). The homolog may also refer to a deletion, insertion, or substitution variant, including an amino acid substitution, thereof and biologically active polypeptide fragments thereof.

To express the neurotrophic factors in the muscle progenitor cells described herein, polynucleotides which encode the factors are ligated into a nucleic acid construct suitable for muscle cell expression. Such a nucleic acid construct includes a promoter sequence for directing transcription of the polynucleotide sequence in the cell in a constitutive or inducible manner.

Constitutive promoters suitable for use with some embodiments of the invention are promoter sequences which are active under most environmental conditions and most types of cells such as the cytomegalovirus (CMV) and Rous sarcoma virus (RSV). Inducible promoters suitable for use with some embodiments of the invention include for example tetracycline-inducible promoter (Zabala M, et al., Cancer Res. 2004, 64(8): 2799-804).

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

As mentioned, the promoter utilized by the nucleic acid construct of some embodiments of the invention is active in the specific cell population transformed—i.e. muscle progenitor cells and more specifically in mature muscle cells. Examples of such promoters include the myosin, actin or skeletal muscle creatine kinase (CK) promoter.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for some embodiments of the invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

In addition to the elements already described, the expression vector of some embodiments of the invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Stratagene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by some embodiments of the invention will depend on the cell type transformed. The ability to select suitable vectors according to the cell type transformed is well within the capabilities of the ordinary skilled artisan and as such no general description of selection consideration is provided herein. For example, bone marrow cells can be targeted using the human T cell leukemia virus type I (HTLV-I) and kidney cells may be targeted using the heterologous promoter present in the baculovirus Autographa californica nucleopolyhedrovirus (AcMNPV) as described in Liang C Y et al., 2004 (Arch Virol. 149: 51-60).

According to one embodiment, a lentiviral vector is used to transfect the muscle cells.

Various methods can be used to introduce the expression vector of some embodiments of the invention into muscle cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et al. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

Other vectors can be used that are non-viral, such as cationic lipids, polylysine, and dendrimers. Nanoparticles are also contemplated.

Other modes of transfection that do not involve integration include the use of minicircle DNA vectors or the use of PiggyBac transposon that allows the transfection of genes that can be later removed from the genome.

The muscle progenitor cells may be genetically modified to express a single neurotrophic factor, to co-express two neurotrophic factors, three neurotrophic factors, four neurotrophic factors or even more neurotrophic factors.

Thus muscle progenitor cells genetically modified to express at least one of GDNF, VEGF, BDNF and IGF-1 are contemplated.

Further, muscle progenitor cells genetically modified to express at least two of GDNF, VEGF, BDNF and IGF-1 are contemplated.

In addition, muscle progenitor cells genetically modified to express at least three of GDNF, VEGF, BDNF and IGF-1 are contemplated.

Further, muscle progenitor cells genetically modified to express each of GDNF, VEGF, BDNF and IGF-1 are also contemplated.

It will be appreciated that various construct schemes can be utilized to express more than one neurotrophic factor from a single nucleic acid construct.

For example, two neurotrophic factors can be co-transcribed as a polycistronic message from a single promoter sequence of the nucleic acid construct. To enable co-translation of both neurotrophic factors from a single polycistronic message, the first and second polynucleotide segments can be transcriptionally fused via a linker sequence including an internal ribosome entry site (TRES) sequence which enables the translation of the polynucleotide segment downstream of the IRES sequence. In this case, a transcribed polycistronic RNA molecule including the coding sequences of both the first and the second neurotrophic factors will be translated from both the capped 5' end and the internal IRES sequence of the polycistronic RNA molecule to thereby produce both the first and the second neurotrophic factors.

Alternatively, the first and second polynucleotide segments can be translationally fused via a protease recognition site cleavable by a protease expressed by the cell to be transformed with the nucleic acid construct. In this case, a chimeric polypeptide translated will be cleaved by the cell expressed protease to thereby generate both the first and the second neurotrophic factors.

Still alternatively, the nucleic acid construct of some embodiments of the invention can include two promoter sequences each being for separately expressing a specific neurotrophic factor of the neurotrophic factors described above. These two promoters which can identical or distinct can be constitutive, tissue specific or regulatable (e.g. inducible) promoters functional in one or more cell types.

It will be appreciated that the present invention also contemplates genetically modifying muscle progenitor cells to express a single neurotrophic factor which are then mixed with a second population of muscle progenitor cells which are genetically modified to express a non-identical neurotrophic factor.

Thus, according to another aspect of the present invention there is provided an isolated cell population, comprising at least four subpopulations of muscle cells, each of the at least four subpopulation being distinct in that they are genetically modified to express a different neurotrophic factor, wherein the neurotrophic factor is selected from the group consisting of glial derived neurotrophic factor (GDNF), insulin growth factor (IGF-1), vascular endothelial growth factor (VEGF) and brain-derived neurotrophic factor (BDNF).

The term "muscle cell" as used herein refers to any cell that contributes to muscle tissue. Myoblasts, satellite cells, myotubes, myofibers, and myofibril tissues are all included in the term "muscle cells". The muscle cell may be comprised within skeletal, cardiac and smooth muscles, particularly within skeletal muscle.

According to a particular embodiment, the muscle cell is a skeletal muscle progenitor cell.

By mixing the subpopulations in different amounts, it is possible to control the ratio of neurotrophic factors in the cell population.

The percentage of cells that express a particular neurotrophic factor may be selected according to the disease for which the cells are intended to treat.

Certain neurotrophic factors or set of neurotrophic factors have been shown to be particularly beneficial for treating a particular disease. For example, cells of the present invention which secrete NT3, IGF1 and BDNF may be particularly suitable for treating ALS.

The present inventors have shown that cell populations which comprise similar amount of cells genetically modified to express one of GDNF, BDNF, VEG-F and IGF-1 (i.e. a mixture of four different cell sub-populations—i.e. MPC-mix, the first genetically modified sub-population to express GDNF, the second genetically modified sub-population to express BDNF, the third genetically modified sub-population to express VEG-F and the fourth genetically modified sub-population to express IGF-1, where each population is present in similar amounts) show improved therapeutic properties (synergism) when compared with cell populations which comprise only one of these cell types for the treatment of ALS and sciatic nerve crush.

The cell populations described herein can be used to treat additional nerve diseases, disorders damage or injury.

The injury or disease may be associated with motor neurons and/or sensory neurons.

According to a particular embodiment, the nerve disease is a neuromuscular disease (spinal muscular atrophy, a amyotrophic lateral sclerosis (ALS), a Werdnig Hoffman disease, a Charcot-Marie tooth disease, multiple sclerosis, myasthenia gravis, muscular dystrophy and a myositis).

According to another embodiment, the nerve disease is a motor neuron disease (e.g. amyotrophic lateral sclerosis (ALS), primary lateral sclerosis (PLS), pseudobulbar palsy and progressive bulbar palsy).

Contemplated nerve damage which may be aided using the cell populations described herein include peripheral nerve injury, peripheral nerve inflammation, autonomic nerve injury, pelvic nerve damage, burn, blunt trauma, back injury, back pain, or sciatica.

Since sensory neurons may also be affected by the neurtotrophic factors described herein, the present invention also contemplates treating pain. The pain may be associated with nerve damage or from other sources—e.g. the pain may be due to a disease such as cancer.

The cells of the present invention can be administered to the treated individual using a variety of transplantation approaches, the nature of which depends on the site of implantation. According to one embodiment, the site of implantation is the muscle.

The term or phrase "transplantation", "cell replacement" or "grafting" are used interchangeably herein and refer to the introduction of the cells of the present invention to target tissue. The cells can be derived from the recipient or from an allogeneic or xenogeneic donor.

For transplanting, the cell suspension is drawn up into the syringe and administered to transplantation recipients. Multiple injections may be made using this procedure.

Typically, the method of the present invention does not require immunosuppression. However, if required, the present invention contemplates encapsulating the muscle cells or administration of immunosuppressive agents.

It will be appreciated that as well as cell therapy for delivery of neurotrophic factors, the present invention also contemplates gene therapy for the transfer of neurotrophic factors such as described by Wang et al., The Journal of Neuroscience, 2002, 22(16):6920-6928; and Acsadi et al., Human Gene Therapy 13:1047-1059,2002, the contents of both being incorporated herein by reference.

Gene therapy as used herein refers to the transfer of genetic material (e.g. DNA or RNA) of interest into a host to treat or prevent a genetic or acquired disease or condition or phenotype. The genetic material of interest encodes a product (e.g. a protein, polypeptide, peptide, functional RNA, antisense) whose production in vivo is desired. For example, the genetic material of interest can encode a neurotrophic factor. For review see, in general, the text "Gene Therapy" (Advanced in Pharmacology 40, Academic Press, 1997).

In in vivo gene therapy, target cells are not removed from the subject rather the genetic material to be transferred is introduced into the cells of the recipient organism in situ, that is within the recipient. These genetically altered cells have been shown to express the transfected genetic material in situ.

To confer specificity, preferably the nucleic acid constructs used to express the polypeptides of the present invention comprise muscle cell-specific promoter sequence elements, as described herein above.

Introduction of nucleic acids by infection in both in vivo therapy offers several advantages over the other listed methods. Higher efficiency can be obtained due to their infectious nature. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

In addition, recombinant viral vectors are useful for in vivo expression of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Retroviral vectors can be constructed to function either as infectious particles or to undergo only a single initial round of infection. In the former case, the genome of the virus is modified so that it maintains all the necessary genes, regulatory sequences and packaging signals to synthesize new viral proteins and RNA. Once these molecules are synthesized, the host cell packages the RNA into new viral particles which are capable of undergoing further rounds of infection. The vector's genome is also engineered to encode and express the desired recombinant gene. In the case of non-infectious viral vectors, the vector genome is usually mutated to destroy the viral packaging signal that is required to encapsulate the RNA into viral particles. Without such a signal, any particles that are formed will not contain a genome and therefore cannot proceed through subsequent rounds of infection. The specific type of vector will depend upon the intended application. The actual vectors are also known and readily available within the art or can be constructed by one skilled in the art using well-known methodology.

Since transduction of cells with conditionally replicating adenoviral vectors is significantly more effective in target cell lysis and spread of viral infection, the nucleic acid construct can include a conditionally replicating adenovirus.

The viral vectors, containing the endothelial cell specific promoters, can also be used in combination with other approaches to enhance targeting of the viral vectors. Such approaches include short peptide ligands and/or bispecific or bifunctional molecule or diabodies (Nettelbeck et al. Molecular Therapy 3:882; 2001).

According to a particular embodiment, the gene therapy is effected such that the gene is not integrated into the genome of the cell. Thus, for example the use of liposomes for the delivery of the neurotrophic factors is also contemplated by the present inventors.

In any of the methods described herein, the cells or the constructs can be administered either per se or, preferably as a part of a pharmaceutical composition that further comprises a pharmaceutically acceptable carrier.

As used herein a "pharmaceutical composition" refers to a preparation of one or more of the chemical conjugates described herein, with other chemical components such as pharmaceutically suitable carriers and excipients. The purpose of a pharmaceutical composition is to facilitate administration of a compound to a subject.

Hereinafter, the term "pharmaceutically acceptable carrier" refers to a carrier or a diluent that does not cause significant irritation to a subject and does not abrogate the biological activity and properties of the administered compound. Examples, without limitations, of carriers are propylene glycol, saline, emulsions and mixtures of organic solvents with water.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

According to a preferred embodiment of the present invention, the pharmaceutical carrier is an aqueous solution of saline.

Techniques for formulation and administration of drugs may be found in "Remington's Pharmaceutical Sciences," Mack Publishing Co., Easton, Pa., latest edition, which is incorporated herein by reference.

Suitable routes of administration include direct administration into the tissue or organ of interest.

For any preparation used in the methods of the invention, the therapeutically effective amount or dose can be estimated initially from in vitro and cell culture assays. Preferably, a dose is formulated in an animal model to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals.

For example, transgenic mice may be used as a model for ALS disease which comprise SOD-1 mutations.

Survival and rotational behavior (e.g. on a rotarod) of the animals may be analyzed (as in Examples 2 and 3) following administration of the cells of the present invention.

The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition, (see e.g., Fingl, et al., 1975, in "The Pharmacological Basis of Therapeutics", Ch. 1 p. 1).

For injection, the active ingredients of the pharmaceutical composition may be formulated in aqueous solutions, preferably in physiologically compatible buffers such as Hank's solution, Ringer's solution, or physiological salt buffer.

Dosage amount and interval may be adjusted individually to levels of the active ingredient which are sufficient to effectively regulate the neurotransmitter synthesis by the implanted cells. Dosages necessary to achieve the desired effect will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or diminution of the disease state is achieved.

The amount of a composition to be administered will, of course, be dependent on the individual being treated, the severity of the affliction, the manner of administration, the judgment of the prescribing physician, etc. The dosage and timing of administration will be responsive to a careful and continuous monitoring of the individual changing condition. For example, a treated ALS's patient will be administered with an amount of cells which is sufficient to alleviate the symptoms of the disease, based on the monitoring indications.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

GENERAL MATERIALS AND METHODS

Protocol for neurotrophic factors secreting muscle progenitor cells preparation: Rat and mouse MPCs were used as a vehicle to introduce vectors expressing growth factors. The MPCs were propagated in a growth medium containing Dulbecco's modified Eagle's medium (DMEM) supplemented with 100 mg/ml streptomycin, 100 U/ml penicillin, 12.5 units/ml nystatin (SPN, Biological Industries, Beit Haemek, Israel), 2 mML-glutamine (Biological Industries), and 10% fetal calf serum (Biological Industries).

The constructs of the neurotrophic genes were generated using ViraPower™ Promoterless Lentiviral Gateway® Kit (Invitrogen, Carlsbad, Calif., USA). The human GDNF, VEGF, IGF-1 and BDNF genes were amplified from the pBluescript plasmids that were purchased from Harvard Institute of Proteomics, Boston, USA, using Plasmid Midi Kit (Qiagen, Valencia, USA). Each of the four genes was inserted into the virus under the CMV promoter in a recombination reaction. For each reaction sample a plasmid containing the CMV promoter was incubated over-night at room temperature with a plasmid containing the DNA, a destination plasmid and the recombination enzyme-LR clonase (Invitrogen). Following establishment of the constructs, they were transformed into One Shot™ Stbl3™ Competent *E. coli* (Invitrogen). 4 µl of the recombination reaction were added to One Shot™ Stbl3™ Competent *E. coli* and were incubated for 30 minutes on ice. After incubation the mix was transferred to 42° C. for 30 seconds and from there to 2 minutes on ice. 250 µl of SOC medium was added to the mix and incubated at 37° C. After one hour, the mix was placed on LB agar plates with ampicillin (Sigma-Aldrich, St. Louis, Mo., USA) for 24 hours at 37° C. On the following day, one colony was picked and DNA was produced using midi kit. For each transfection sample, 4 µg DNA (of each gene separately) were diluted in 1.5 ml Opti-MEM (Biological industries). Lipofectamaine 2000 (Invitrogen) was diluted in 1.5 ml Opti-MEM. After 5 minutes of room temperature incubation, the diluted mix and DNA with the diluted Lipofectamine 2000 were combined and incubated for 20 minutes in room temperature. After incubation, the 3 ml of complexes were added to flasks containing 95% confluent MPCs cultured in an antibiotic free medium and incubated at 37° C. in a $CO_2$ incubator. Six hours later, the cells' media was replaced with their regular growth medium. On the next day, 4 mg/ml of Blastocidin was added to the cells for selection for two weeks.

Immunocytochemistry of muscle progenitor cells: Cells grown on coverslips were fixed with 4% paraformaldehyde for 10 minutes, washed with phosphate-buffered saline (PBS), and then incubated in a blocking and permeabilization solution (5% normal goat serum, 1% bovine serum albumin, and 0.5% Triton X-100 in PBS) and incubated with a primary antibody overnight at 4° C. After being washed with PBS, cells were incubated with an Alexa-conjugated secondary antibody. The nuclei were counterstained with 4,6-diamidino-2-phenylindole (DAPI; 1:500; Sigma-Aldrich). The following primary antibodies were used: rabbit α-BDNF (1:100; Santa Cruz Biotechnology Inc., Santa Cruz, Calif., USA), rabbit α-GDNF (1:100; Santa Cruz Biotechnology), mouse α-IGF-1 (1:100; Santa Cruz Biotechnology), and mouse α-VEGF (1:100; Santa Cruz Biotechnology). Secondary antibodies were Alexa Fluor 488 (1:500; Invitrogen) and Alexa Fluor 568 (1:500; Invitrogen).

The quantification of positive cells was performed on five random fields photographed at a magnification of X100, as a percentage of the positive cells from the number of total DAPI-positive nuclei.

ELISA analysis: Cell supernatant pre- and post-transfection was collected, frozen, and quantified. An enzyme-linked immunosorbent assay (ELISA) kit (R&D systems, Minneapolis, Minn., USA) was used to detect the presence of each one of the secreted neurotrophic factors. The assay was conducted according to the manufacturer's protocol in triplicate, and results were read at wavelengths of 450/550 using an ELISA reader (Powerwave X; Biotek Instruments, Winooski, Vt., USA). Results were compared between the cells' media before and after transfection.

Cell viability assay: The MPCs conditioned media was tested for its ability to protect motor neurons cell-line (NSCs-34) from hypoxic stress. NSCs-34 were placed in hypoxic environment for 48 hours together with the conditioned media of each of the cloned MPCs expressing one of the four NTFs, combination of MPCs-NTF, MPCs-GFP, MPCs growth media or serum free growth media.

After 48 hours, Alamar blue 10% (AbD serotec, Kidlington, UK) was added to the cells for 6 hours. The assay was conducted in triplicate, and results were read at wavelengths of 590 nm using fluostar device. Results were normalized to cells under the same treatments in normoxia.

The sciatic nerve crush model in rats: The sciatic nerve crush model was applied on male Wistar rats (Harlan, Jerusalem) weighing 230-250 g. Rats were placed under 12-hour-light/12-hour-dark conditions and grown in individually ventilated cages (IVC) with ad libitum access to food and water. Rats were anesthetized with Chloral hydrate 7 mg/ml (Sigma-Aldrich, St. Louis). The right sciatic nerve was exposed and a vessel clamp was applied 10 mm above the first branching of the nerve, for 30 seconds.

One day after surgery, the control group was injected with 100 µl PBS into the lesion site (n=9). The second control group was injected with $10^6$ rMPCs-GFP cells suspended in 100 µL PBS into the lesion site (n=9). Four treatment groups were injected with $10^6$ rMPCs-BDNF/rMPCs-GDNF/rMPCs-IGF-1/rMPCs-VEGF cells suspended in 100 µl PBS and the fifth treatment group was injected with a combination of all rMPCs-NTFs cells—$25 \times 10^4$ cells from rMPCs-BDNF, rMPCs-GDNF, rMPCs-IGF-1, and rMPCs-VEGF (a total of $10^6$ cells, n=9).

Rat motor function measurements: Rats were examined for motor functioning twice a week, one week prior to injury and three weeks following injury. Motor activity was measured by the (San Diego instruments, USA) test. In this test, following a brief training period, adult wild-type rats are able to remain balanced on a rotating rod in accelerated speed, from 0 to 25 RPM for up to 4 minutes. After a sciatic nerve crush, the rat's ability of balancing is damaged and the animal falls off the rod after shorter periods of time. The machine has a laser beam that detects the fall [7-8]. The average of three consecutive runs from each session on the Rotarod were assessed and the groups' performance was compared.

Electrophysiological study: Compound muscle action potential (CMAP) amplitudes were recorded from the sciatic innervated cranial tibial muscles following electric stimulation of the sciatic nerve. An active monopolar needle electrode was placed over the sciatic nerve at the sciatic notch and a supramaximal intensity electric stimulus of 0.1 ms duration was applied. An average of ten consecutive runs from each measurement was documented. The CMAP amplitudes were converted to the ratios of the measurements taken at the injured side, divided by those of the normal side to adjust for the effect of the anesthesia, muscle masses and other physical variations between rats [32-33].

Immunohistochemistry of rat muscle cells: Hind limb muscles of rats were removed and frozen in liquid nitrogen, 15 days after transplantation. Muscles were sectioned at 20 μm using a cryostat (Leica CM1850) and placed on glass slides for staining. The sections were fixed with 4% paraformaldehyde for 30 minutes, washed with phosphate-buffered saline (PBS), and then incubated in a blocking and permeabilization solution (5% normal goat serum, 1% bovine serum albumin, and 0.5% Triton X-100 in PBS) and incubated with a primary antibody overnight at 4° C. After being washed with PBS, cells were incubated with an Alexa-conjugated secondary antibody. The nuclei were counterstained with 4,6-diamidino-2-phenylindole (DAPI; 1:500; Sigma-Aldrich). The antibodies used were the same as described for the muscle progenitor cells.

Assessment of neuromuscular junction innervations: Endplate innervation was marked by alpha-bungarotoxin and synaptophysin as described previously [34]. Hind limb muscles were dissected and frozen in liquid nitrogen. Muscles were sectioned at 20 μm using a cryostat and placed on glass slides for staining. The sections were fixed with 4% PFA-PBS and labeled with alpha-bungarotoxin conjugated with fluorescence marker Alexa Fluor 594 (1:1000, Invitrogen, CA, USA) and anti-synaptophysin (rabbit polyclonal, 1:100, Santa Cruz Biotechnology, Santa Cruz, USA) antibodies overnight at 4° c. After washing with PBS, the sections were incubated with anti-rabbit Alexa Fluor 488-conjugated antibody (1:1,000, Invitrogen) for one hour at room temperature followed by washes, and covered with cover glasses using aqueous mounting medium (Invitrogen). NMJs were classified into two groups based on the degree of innervation of postsynaptic receptor plaques by nerve terminals [34]. Endplates were scored as "innervated" if there was overlap with the axon terminal, or "denervated" if the end-plate was not associated with an axon [34].

SOD1-G93A transgenic mice model for ALS: The colony of SOD1-G93A transgenic mice (SOD1 mice) was obtained from the Jackson Laboratory (USA). The mice were bred with SJL mice. Mice were placed under 12-hour-light/12-hour-dark conditions and grown in individually ventilated cages (IVC) with ad libitum access to food and water.

At the age of 90 and 120 days, mMPCs were transplanted into the gastrocnemius medial and lateral muscles ($5 \times 10^5$ cells in 25 ul PBS into each hindlimb). The control group was injected with 25 μl PBS into the lesion site (n=24, 12 males and 12 females). The second control group was injected with $5 \times 10^5$ mMPCs-GFP cells suspended in 25 μL PBS into the lesion site (n=24, 12 males and 12 females). The third group was injected with $5 \times 10^5$ mIVIPCs-GDNF suspended in 100 μl PBS and the fourth group was injected with a combination of all mMPCs-NTFs cells—$1.25 \times 10^5$ cells from mMPCs-BDNF, mMPCs-GDNF, mMPCs-IGF-1, and mMPCs-VEGF (a total of $5 \times 10^5$ cells, n=24, 12 males and 12 females).

Mice motor function measurements by rotorod: Mice were examined for motor functioning once a week, starting from the age of 80 days. Motor activity was measured by the (San Diego instruments) test. In this test, following a brief training period, adult wild-type mice are able to remain balanced on a rotating rod in accelerated speed, from 0 to 25 RPM for up to 4 minutes. With time, SOD1 mice weaken, their ability to balance is damaged and they fall off the rod after shorter periods of time. The machine has a laser beam that detects the fall [7-8]. The average of three consecutive runs from each session was assessed and the groups' performance was compared.

Statistical Analysis: The results are expressed as means±SE. The one way ANOVA test was used to compare the three groups. Statistical calculations were performed using SPSS, version 13 (SPSS, Chicago, USA).

Example 1

Characterization of Neurotrophic Factor (NTF) Transfected Muscle Progenitor Cells (MPCs)
RESULTS Using an immunocytochemical study and ELISA analysis, the protein expression and secretion of neurotrophic factors was measured following gene transfection. It was found that 100% of the genetically manipulated MPCs had a strong positive expression of BDNF, GDNF, IGF-1, and VEGF. The secretion and the presence of BDNF, GDNF, IGF-1, and VEGF in the mediaprior to and following transfection was analyzed using ELISA kit. High levels of the four neurotrophic factors were demonstrated compared with untransfected MPCs (FIGS. 1A-K).

After 48 hours of culture in an hypoxic environment, the viability of the cells of the motor neuron cell-line NSCs-34 decreased. However, cells that were cultured in the MPC-NTF conditioned media were protected (FIGS. 2A-C). Results presented as ratio from normoxic conditions.

Example 2

Rats Improved Motor Function After Cell Transplantation

All rats suffered from a right hind limb limp after crush and their motor function deteriorated. All the rat groups performed equally well on the rotorod prior to the injury. However, immediately following the crush, the performance of rats markedly declined by 60%. Three days later, PBS treated rats demonstrated poor motor function (98.5±4.6 seconds on rotorod) while the singly transfected MPCs (GFP/BDNF/GDNF/IGF-1/VEGF) treated rats showed a moderate improvement (125±12.5; 152±9.7; 129±11.2; 129±13.4; 121±9.7, respectively). When a mixture of all four NTF transfected MPCs were transplanted, the rats demonstrated significant better motor performance (183.8±5.3, p<0.05). The same trend was observed six and eight days after the crush (FIG. 3).

Example 3

Electrophysiology Study Indicates Axonal Regeneration in MPCs-NTFs Treated Rats

Decreased compound muscle action potential (CMAP) was observed immediately following the sciatic crush in all the groups when compared to the non-injured contra lateral side. Four days following the surgery, while the average ratio of CMAP, prior to the transplantation and following the transplantation, in the singly transfected MPCs-(GFP/BDNF/GDNF/IGF-1/VEGF) showed a poor increase in CMAP amplitude (0.2±0.12; 0.26±0.09; 0.12±0.04; 0.32±0.16; 0.26±0.07, respectively), a significantly improved CMAP ratio of 0.4±0.09 was found in the group transplanted with a mixture of all four NTF transfected MPCs (FIG. 4).

Example 4

MPCs-NTFs Inhibited NMJs Denervation

Two weeks following sciatic nerve crush, NMJs were analyzed within the crush area and the gastocnemios and tibialis muscles. Double stained endplates, with acetylcholine receptor ligand, alpha bungarotoxin and antibodies against the post synaptic protein, synptophysin, were counted as innervated NMJ. After examining over 100 stained slides, 69%±12 preservation of innervated NMJs in the injured gastocnemios and tibialis muscles was observed, as compared to the uninjured hind limb. In contrast, rats transplanted with a mixture of all four NTF transfected MPCs showed higher preservation (89%±1.5) of the innervated NMJ compared to the uninjured limbs (FIGS. 5A-B).

Example 5

MPC Expressing NTF Can Be Detected in the Muscles Two Weeks After Transplantation Histology of the rats' hind limb muscles two weeks following transplantation using immunostaining with specific antibodies revealed high levels of BDNF, GDNF, IGF-1, and VEGF in MPCs-NTFs and their surrounding muscles tissue. There was no sign of tumor formation in the transplanted area (FIG. 6A-D).

Example 6

MPCs-NTFs Delayed Motor Function Reduction in Treated SOD1 Transgenic Mice

The mice motor performance was evaluated by the rotorod test once a week, beginning at 70 days of age. At 70 days, there was no significant difference among experimental groups. The mice were transplanted on day 90 and 110 and the motor function was followed every week on rotarod. In the control group (PBS injections) the average of 50% reduction in the performance on rotarod can be seen on day 116 comparable to the MPC-GFP and MPC-GDNF (115 and 116 respectively). However, the 50% reduction in motor function in the mice transplanted with a mixture of all four NTF transfected MPCs was significantly delayed to the age of 124 days. Notably this effect was found only in the females groups while the male groups show similar behavior (FIGS. 7A-B).

Example 7

MPCs-NTFs Prolonged Life Span of Treated SOD1 Transgenic Mice

Life spans of SOD1 transgenic mice rats transplanted with a mixture of all four NTF transfected MPCs were significantly prolonged compared with either Saline/MPCs-GFP or MPCs-GDNF treated SOD1 mice. SOD1 transgenic mice rats transplanted with a mixture of all four NTF transfected MPCs lived an average of 137.64+2.19 days, whereas saline/MPCs-GFP or MPCs-GDNF treated mice lived an average of 129.58+1.46; 125.38+1.47; 129.4+0.92 respectively. Notably this effect was demonstrate only in females (FIGS. 8A-B).

In another experiment mice were obtained by breeding SOD1 mice from Jackson laboratories (based on SJL strain background) with C57/bl mice. These mice are more suitable for transplantation with the genetically modified mouse MPC which were isolated from ROSA-26 mice which express ubiquitously Beta-gal and share C57/B1 background. In order to increase the efficiency of incorporation of the inoculated cells into multinucleated fibers, the muscles were preconditioned by injection of minimal amounts of cardiotoxin, delivered one day prior to transplantation. This treatment enhances fusion of the transplanted MPC with host myogenic cells, forming post mitotic multinucleated fibers. Indeed, these modifications dramatically improved the efficiency of the MPC-MIX. Higher performance on rotarode of the MPC-MIX transplanted mice group was observed as compared to the saline treated mice (FIG. 9A). Moreover, a significant delay in the onset of the symptoms (defined as more than 20% reduction on rotarod) in mice transplanted with the MPC-MIX was observed. While in the saline-treated group less than 50% of the mice are free of symptoms on day 109, in the MPC-MIX treated mice 50% of mice are free of symptoms at least 39 later, on day 150 (FIG. 9B).

Example 8

MPC-NTF Conditioned Media Synergistically Increase AKT Phosphorylation

In order to study the possible synergistic effect of the MPC-MIX on a known signal transduction pathway, the present inventors focused on the PI3K-AKT pathway which is involved in cell survival, following application of the four NTFs conditioned media. Thus, motor neuron cell line (NSC-34) were placed in a hypoxic environment for 24 hours in the presence of conditioned media of each of the cloned MPCs expressing one of the four NTF, MPCs-MIX+, or control growth medium. After 24 hours, cell's protein extraction was subject to Western blot analysis for the ratio of AKT vs. phosphorylated-AKT proteins. The ratio was calculated for each treatment (FIG. 10). This analysis demonstrated that phosphorylated AKT was undetectable in the untreated cells (control medium) while the ratio in the presence of MPC-BDNF/GDNF/IGF-1 was 0.11, 0.09 and 0.12 respectively. In contrast, the MPC-MIX treatment increased the phosphorylated AKT ratio to 6-8 folds higher (0.73).

REFERENCES

1. Frey D, Schneider C, Xu L, Borg J, Spooren W, Caroni P (2000) Early and selective loss of neuromuscular synapse subtypes with low sprouting competence in motoneuron diseases. J Neurosci 20:2534-2542.
2. Fischer L R, Culver D G, Tennant P et al (2003) Amyotrophic lateral sclerosis is a distal axonopathy: evidence in mice and man. Exp Neurol 185:232-240.
3. Fryer, H. J., Wolf, D. H., Knox, R. J., Strittmatter, S. M., Pennica, D., O'Leary, R. M., et al. (2000). Brain-derived neurotrophic factor induces excitotoxic sensitivity in cultured embryonic rat spinal motor neurons through activation of the phosphatidylinositol 3-kinase pathway. Journal of neurochemistry, 74 (2): 582-95.
4. Hu, P., & Kalb, R. G. (2003). BDNF heightens the sensitivity of motor neurons to excitotoxic insults through activation of TrkB. Journal of neurochemistry, 84(6): 1421-30.
5. Mousavi, K., Parry, D. J., & Jasmin, B. J. (2004). BDNF rescues myosin heavy chain IIB muscle fibers after neonatal nerve injury. American journal of physiology, 287 (1): C22-9.

6. Ozdinler, P. H., & Macklis, J. D. (2006). IGF-I specifically enhances axon outgrowth of corticospinal motor neurons. Nature neuroscience, 9(11): 1371-81.
7. Acsadi, G., Anguelov, R., Yang, H., Toth, G., Thomas, R., Jani, A., et al. (2002). Increased survival and function of SOD1 mice after Glial cell-derived neurotrophic factor gene therapy. Human Gene Therapy, 10 (13):1047-1059.
8. Mohajeri, H., Figlewicz, D., & Bohn, M., (1999). Intramuscular grafts of myoblasts genetically modified to secrete glial cell iine-derived neurotrophic factor prevent motoneuron loss and disease progression in a mouse model of familial amyotrophic lateral sclerosis. Human Gene Therapy, 10: 1853-1866.
9. Sakowski, S. A., Schuyler, A. D., & Feldman, E. L. (2009). Insulin-like growth factor-I for the treatment of amyotrophic lateral sclerosis. Amyotrophic lateral sclerosis: official publication of the World Federation of Neurology Research Group on Motor Neuron Diseases, 10(2): 63-73.
10. Dobrowolny, G., Giacinti, C., Pelosi, L., Nicoletti, C., Winn, N., Barberi, L., et al. (2005). Muscle expression of a local Igf-1 isoform protects motor neurons in an ALS mouse model. The journal of cell biology, 168(2): 193-9.
11. Li, W., Brakefield, D., Pan, Y., Hunter, D., Myckatyn, T. M., & Parsadanian, A. (2007). Muscle-derived but not centrally derived transgene GDNF is neuroprotective in G93A-SOD1 mouse model of ALS. Experimental neurology, 203(2): 457-71.
12. Musarò, A., McCullagh, K., Paul, A., Houghton, L., Dobrowolny, G., Molinaro, M., et al. (2001). Localized Igf-1 transgene expression sustains hypertrophy and regeneration in senescent skeletal muscle. Nature genetics, 27(2): 195-200.
13. Rabinovsky, E. D., Gelir, E., Gelir, S., Lui, H., Kattash, M., DeMayo, F. J., et al. (2003). Targeted expression of IGF-1 transgene to skeletal muscle accelerates muscle and motor neuron regeneration. The FASEB journal: official publication of the Federation of American Societies for Experimental Biology, 17(1):53-5.
14. Crone, S. A., & Lee, K. F. (2002). Gene targeting reveals multiple essential functions of the neuregulin signaling system during development of the neuroendocrine and nervous systems. Annals of the New York Academy of Sciences, 971: 547-53.
15. Azzouz, M., Ralph, G. S., Storkebaum, E., Walmsley, L. E., Mitrophanous, K. A., Kingsman, S. M., et al. (2004). VEGF delivery with retrogradely transported lentivector prolongs survival in a mouse ALS model. Nature 429 (6990): 413-7.
16. Wang, Y., Mao, X. O., Xie, L., Banwait, S., Marti, H. H., Greenberg, D. A., et al. (2007). Vascular endothelial growth factor overexpression delays neurodegeneration and prolongs survival in amyotrophic lateral sclerosis mice. The Journal of neuroscience: the official journal of the Society for Neuroscience, 27(2): 304-7.
17. Storkebaum, E., Lambrechts, D., Dewerchin, M., Moreno-Murciano, M. P., Appelmans, S., Oh, H., et al. (2005). Treatment of motoneuron degeneration by intracerebroventricular delivery of VEGF in a rat model of ALS. Nature neuroscience, 8(1): 85-92.
18. Zheng, C., Sköld, M. K., Li, J., Nennesmo, I., Fadeel, B., & Henter, J. I. (2007). VEGF reduces astrogliosis and preserves neuromuscular junctions in ALS transgenic mice. Biochemical and biophysical research communications, 363(4): 989-93.
19. Yaffe, D. (1968). Retention of differentiation potentialities during prolonged cultivation of myogenic cells. Proc Natl Acad Sci USA, 61(2): 477-83.
20. Yaffe, D. (1969). Cellular aspects of muscle differentiation in vitro. Curr Top Dev Biol, 4: 37-77.
21. Yaffe, D. & Saxel, O. (1977). Serial passaging and differentiation of myogenic cells isolated from dystrophic mouse muscle. Nature, 270 (5639): 725-7.
22. Konstantinou, K., & Dunn, K. M. (2008). Sciatica: review of epidemiological studies and prevalence estimates. Spine, 33 (22):2464-2472.
23. Dadon-Nachum, M., Sadan, O., Srugo, I., Melamed, E., & Offen, D. (2011). DDifferentiated mesenchymal stem cells for sciatic nerve injury. Stem Cell Rev, Epub ahead of print.
24. Gonzales de Aguilar, J. L., Echaniz-Laguna, A., Fergani, A., Rene, F., Meininger V., et al. (2007). Amyotrophic lateral sclerosis: all roads lead to Rome. J Neurochem, 101: 1153-60.
25. Bruijn, L., Miller, T. M., & Cleveland, D. W. (2004). Unraveling the mechanisms involved in motor neuron degeneration in ALS. Annu Rev Neurosci, 27: 723-749.
26. Lev, N., Ickowicz, D., Barhum, Y., Melamed, E., & Offen, D. (2009). DJ-1 changes in G93A-SOD1 transgenic mice: Implications for oxidative stress in ALS. J Mol Neurosci, 38:94-102.
27. Offen, D., Barhum, Y., Melamed, E., Embacher, N., Schindler, C., & Ransmayr, G., (2009). Spinal cord mRNA profile in patients with ALS: comparison with transgenic mice expressing the human SOD-1 mutant. Journal of Molecular Neuroscience, 38 (2): 85-93.
28. Séverine, B., Velde, C. V., & Cleveland, D. W. (2006). ALS: a disease of motor neurons and their nonneuronal neighbors. Neuron, 52: 39-59.
29. Ilieva, E. V., Ayala, V., Jové, M., Dalfo, E., Cacabelos, D., et al. (2007). Oxidative and endoplasmic reticulum stress interplay in sporadic amyotrophic lateral sclerosis. Brain, 130: 3111-23.
30. Gruzman, A., Wood, W. L., Alpert, E., Prasad, M. D., Miller, R. G., et al. (2007). Common molecular signature in SOD-1 for both sporadic and familial amyotrophic lateral sclerosis. Proc Natl Acad Sci USA 104:12524-9.
31. Turner, B. J., & Talbot, K. (2008). Transgenics, toxicity and therapeutics in rodent models of mutant SOD-1-mediated familial ALS. Prog Neurobiol, 85:94-134.
32. Pan, H. C., Yang, D. Y., Chiu, Y. T., Lai, S. Z., Wang, Y. C., Chang, M. H., et al. (2006). Enhanced regeneration in injured sciatic nerve by human amniotic mesenchymal stem cells. Journal of clinical neuroscience, 13: 570-575.
33. Pan, H. C., Cheng, F. C., Chen, C. J., Lai, S. Z., Lee, C. W., Yang, D. Y., et al. (2007). Post injury regeneration in rat sciatic nerve facilitated by neurotrophic factors secreted by amniotic fluid mesenchymal stem cells. Journal of clinical neuroscience, 14: 1089-1098.
34. Kim, S., Honmou, O., Kato, K., Nonaka, T., Houkin, K., Hamada, H, et al. (2006). Neuronal differentiation potential of peripheral blood and bone marrow derived precursor cells. Brain research, 1123: 27-33.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An isolated cell population, comprising at least four subpopulations of human muscle progenitor cells, each of the at least four subpopulations being distinct in that they are genetically modified to express a different neurotrophic factor, wherein the neurotrophic factor is selected from the group consisting of glial derived neurotrophic factor (GDNF), insulin growth factor (IGF-1), vascular endothelial growth factor (VEGF) and brain-derived neurotrophic factor (BDNF).

2. The isolated cell population of claim 1, wherein said muscle progenitor cells comprise skeletal muscle progenitor cells.

3. The isolated cell population of claim 1, wherein each of said at least four subpopulations are present in substantially equal amounts.

4. The isolated cell population of claim 1, wherein each of said at least four subpopulations is genetically modified to express a single neurotrophic factor.

* * * * *

SEQUENCE LISTING

```
<160> NUMBER OF SEQ ID NOS: 22

<210> SEQ ID NO 1
<211> LENGTH: 485
<212> TYPE: DNA
<213> ORGANISM: Homo sapiens

<400> SEQUENCE: 1
caaatatgcc agaggattat cctgatcagt tcgatgatgt catggatttt attcaagcca      60
ccattaaaag actgaaaagg tcaccagata acaaatggc agtgcttcct agaagagagc     120
ggaatcggca ggctgcagct gccaacccag agaattccag aggaaaaggt cggagaggcc     180 agagggggcaa aaaccgggt tgtgtcttaa ctgcaataca tttaaatgtc actgacttgg     240
gtctgggcta tgaaaccaag gaggaactga ttttaggta ctgcagcggc tcttgcgatg     300
cagctgagac aacgtacgac aaaatattga aaacttatc cagaaataga aggctggtga     360
gtgacaaagt agggcaggca tgttgcagac ccatcgcctt tgatgatgac ctgtcgtttt     420
tagatgataa cctggtttac catattctaa gaaagcattc cgctaaaagg tgtggatgta     480
tctga                                                                 485

<210> SEQ ID NO 2
<211> LENGTH: 211
<212> TYPE: PRT
<213> ORGANISM: Homo sapiens

<400> SEQUENCE: 2

Met Lys Leu Trp Asp Val Val Ala Val Cys Leu Val Leu Leu His Thr
1               5                   10                  15

Ala Ser Ala Phe Pro Leu Pro Ala Gly Lys Arg Pro Pro Glu Ala Pro
            20                  25                  30

Ala Glu Asp Arg Ser Leu Gly Arg Arg Ala Pro Phe Ala Leu Ser
        35                  40                  45

Ser Asp Ser Asn Met Pro Glu Asp Tyr Pro Asp Gln Phe Asp Val
    50                  55                  60

Met Asp Phe Ile Gln Ala Thr Ile Lys Arg Leu Lys Arg Ser Pro Asp
65                  70                  75                  80

Lys Gln Met Ala Val Leu Pro Arg Arg Glu Arg Asn Arg Gln Ala Ala
                85                  90                  95

Ala Ala Asn Pro Glu Asn Ser Arg Gly Lys Gly Arg Arg Gly Gln Arg
            100                 105                 110

Gly Lys Asn Arg Gly Cys Val Leu Thr Ala Ile His Leu Asn Val Thr
        115                 120                 125

Asp Leu Gly Leu Gly Tyr Glu Thr Lys Glu Glu Leu Ile Phe Arg Tyr
    130                 135                 140

Cys Ser Gly Ser Cys Asp Ala Ala Glu Thr Thr Tyr Asp Lys Ile Leu
145                 150                 155                 160

Lys Asn Leu Ser Arg Asn Arg Arg Leu Val Ser Asp Lys Val Gly Gln
```

```
                165                 170                 175
Ala Cys Cys Arg Pro Ile Ala Phe Asp Asp Asp Leu Ser Phe Leu Asp
                180                 185                 190

Asp Asn Leu Val Tyr His Ile Leu Arg Lys His Ser Ala Lys Arg Cys
            195                 200                 205

Gly Cys Ile
    210

<210> SEQ ID NO 3
<211> LENGTH: 883
<212> TYPE: DNA
<213> ORGANISM: Homo sapiens

<400> SEQUENCE: 3
tgccatggtt acttttgcca cgatcttaca ggtgaacaag gtgatgtcca tcttgtttta      60
tgtgatattt ctcgcttatc tccgtggcat ccaaggtaac aacatggatc aaaggagttt     120
gccagaagac tcgctcaatt ccctcattat taagctgatc caggcagata ttttgaaaaa     180
caagctctcc aagcagatgg tggacgttaa ggaaaattac cagagcaccc tgcccaaagc     240
tgaggctccc cgagagccgg agcggggagg gcccgccaag tcagcattcc agccagtgat     300
tgcaatggac accgaactgc tgcgacaaca gagacgctac aactcaccgc gggtcctgct     360
gagcgacagc accccttgg agccccgcc cttgtatctc atggaggatt acgtgggcag      420
ccccgtggtg gcgaacagaa catcacggcg aaacggtac gcggagcata agagtcaccg     480
agggagtac tcggtatgtg acagtgagag tctgtgggtg accgacaagt catcggccat      540
cgacattcgg ggacaccagg tcacggtgct gggggagatc aaaacgggca actctcccgt     600
caaacaatat ttttatgaaa cgcgatgtaa ggaagccagg ccggtcaaaa acggttgcag     660
gggtattgat gataaacact ggaactctca gtgcaaaaca tcccaaacct acgtccgagc     720
actgacttca gagaacaata aactcgtggg ctggcggtgg atacggatag acacgtcctg     780
tgtgtgtgcc ttgtcgagaa aaatcggaag aacatgaatt ggcatctctc cccatatata     840
aattattact ttaaattata tgatatgcat gtagcatata aat                        883

<210> SEQ ID NO 4
<211> LENGTH: 257
<212> TYPE: PRT
<213> ORGANISM: Homo sapiens

<400> SEQUENCE: 4

Met Ser Ile Leu Phe Tyr Val Ile Phe Leu Ala Tyr Leu Arg Gly Ile
1               5                   10                  15

Gln Gly Asn Asn Met Asp Gln Arg Ser Leu Pro Glu Asp Ser Leu Asn
            20                  25                  30

Ser Leu Ile Ile Lys Leu Ile Gln Ala Asp Ile Leu Lys Asn Lys Leu
        35                  40                  45

Ser Lys Gln Met Val Asp Val Lys Glu Asn Tyr Gln Ser Thr Leu Pro
    50                  55                  60

Lys Ala Glu Ala Pro Arg Glu Pro Glu Arg Gly Gly Pro Ala Lys Ser
65                  70                  75                  80

Ala Phe Gln Pro Val Ile Ala Met Asp Thr Glu Leu Leu Arg Gln Gln
                85                  90                  95

Arg Arg Tyr Asn Ser Pro Arg Val Leu Leu Ser Asp Ser Thr Pro Leu
            100                 105                 110

Glu Pro Pro Pro Leu Tyr Leu Met Glu Asp Tyr Val Gly Ser Pro Val
```

```
                115                 120                 125
Val Ala Asn Arg Thr Ser Arg Arg Lys Arg Tyr Ala Glu His Lys Ser
            130                 135                 140

His Arg Gly Glu Tyr Ser Val Cys Asp Ser Glu Ser Leu Trp Val Thr
145                 150                 155                 160

Asp Lys Ser Ser Ala Ile Asp Ile Arg Gly His Gln Val Thr Val Leu
                165                 170                 175

Gly Glu Ile Lys Thr Gly Asn Ser Pro Val Lys Gln Tyr Phe Tyr Glu
            180                 185                 190

Thr Arg Cys Lys Glu Ala Arg Pro Val Lys Asn Gly Cys Arg Gly Ile
        195                 200                 205

Asp Asp Lys His Trp Asn Ser Gln Cys Lys Thr Ser Gln Thr Tyr Val
        210                 215                 220

Arg Ala Leu Thr Ser Glu Asn Asn Lys Leu Val Gly Trp Arg Trp Ile
225                 230                 235                 240

Arg Ile Asp Thr Ser Cys Val Cys Ala Leu Ser Arg Lys Ile Gly Arg
                245                 250                 255

Thr

<210> SEQ ID NO 5
<211> LENGTH: 1335
<212> TYPE: DNA
<213> ORGANISM: Homo sapiens

<400> SEQUENCE: 5
ggggctgccg ccgccgcgcc cgggcgaccc gcccgctcgc tgtcccgcgc accccgtagc      60
gcctcgggct cccgggccgg acagaggagc ccggtgcgcc cctccacctc ctgctcgggg    120
ggctttaatg agacacccac cgctgctgtg gggccggcgg ggagcagcac cgcgacgggg    180
accggggctg ggcgctggag ccagaatcgg aaccacgatt tgactccgcc gccggggacc    240
cgtgagtttg tgtggacccc gagttccacc aggtgagaag agtgatgacc atccttttcc    300
ttactatggt tatttcatac tttggttgca tgaaggctgc ccccatgaaa gaagcaaaca    360
tccgaggaca aggtggcttg gcctacccag gtgtgcggac ccatgggact ctggagagcg    420
tgaatgggcc caaggcaggt tcaagaggct tgacatcatt ggctgacact ttcgaacacg    480
tgatagaaga gctgttggat gaggaccata aagttcggcc caatgaagaa acaataaggg    540
acgcagactt gtacacgtcc agggtgatgc tcagtagtca agtgcctttg gagcctcctc    600
ttctctttct gctggaggaa tacaaaaatt acctagatgc tgcaaacatg tccatgatgg    660
tcctgcgcca ctctgacccc tgcccgccgag gggagctgag cgtgtgtgac agtattagtg    720
agtgggtaac ggcggcagac aaaaagactg cagtggacat gtcgggcggg acggtcacag    780
tccttgaaaa ggtccctgta tcaaaaggcc aactgaagca atacttctac gagaccaagt    840
gcaatcccat gggttacaca aaagaaggct gcaggggcat agacaaaagg cattggaact    900
cccagtgccg aactacccag tcgtacgtgc gggcccttac catggatagc aaaaagagaa    960
ttggctggcg attcataagg atagacactt cttgtgtatg tacattgacc attaaaaggg   1020
gaagatagtg gatttatgtt gtatagatta gattatattg agacaaaaat tatctatttg   1080
tatatataca taacagggta aattattcag ttaagaaaaa aataatttta ttaactgcat   1140
gtataaatga agtttataca gtacagtggt tctacaatct atttattgga catgtccatg   1200
accagaaggg aaacagtcat ttgcgcacaa cttaaaaagt ctgcattaca ttccttgata   1260
atgttgtggt ttgttgccgt tgccaagaac tgaaaacata aaaatttaaa aaaaataatc   1320
```

```
ccttgcatgc tgccc                                              1335
```

<210> SEQ ID NO 6
<211> LENGTH: 247
<212> TYPE: PRT
<213> ORGANISM: Homo sapiens

<400> SEQUENCE: 6

| Met | Thr | Ile | Leu | Phe | Leu | Thr | Met | Val | Ile | Ser | Tyr | Phe | Gly | Cys | Met |
|---|---|---|---|---|---|---|---|---|---|---|---|---|---|---|---|
| 1 | | | | 5 | | | | | 10 | | | | | 15 | |

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp His Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Met Val Leu Arg
        115                 120                 125

His Ser Asp Pro Ala Arg Arg Gly Glu Leu Ser Val Cys Asp Ser Ile
    130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
        195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
225                 230                 235                 240

Leu Thr Ile Lys Arg Gly Arg
                245

<210> SEQ ID NO 7
<211> LENGTH: 1020
<212> TYPE: DNA
<213> ORGANISM: Homo sapiens

<400> SEQUENCE: 7

```
taacacagac tcagctgcca gagcctgctc ttaacacctg tgtttccttt tcagatctta    60
caggtgaaca aggtgatgtc catcttgttt tatgtgatat ttctcgctta tctccgtggc   120
atccaaggta caacatggat caaaggagt tgccagaag actcgctcaa ttccctcatt     180
attaagctga tccaggcaga tattttgaaa acaagctct ccaagcagat ggtggacgtt    240
aaggaaaatt accagagcac cctgcccaaa gctgaggctc cccgagagcc ggagcgggga   300
gggcccgcca agtcagcatt ccagccggtg attgcaatgg acaccgaact gctgcgacaa   360
```

-continued

```
cagagacgct acaactcacc gcgggtcctg ctgagcgaca gcaccccctt ggagccccg      420 cccttgtatc tcatggagga ttacgtgggc agccccgtgg tggcgaacag aacatcacgg      480
cggaaacggt acgcggagca taagagtcac cgaggggagt actcggtatg tgacagtgag      540
agtctgtggg tgaccgacaa gtcatcggcc atcgacattc ggggacacca ggtcacggtg      600
ctgggggaga tcaaaacggg caactctccc gtcaaacaat atttttatga aacgcgatgt      660
aaggaagcca ggccggtcaa aaacggttgc aggggtattg atgataaaca ctggaactct      720
cagtgcaaaa catcccaaac ctacgtccga gcactgactt cagagaacaa taaactcgtg      780
ggctggcggt ggatacggat agacacgtcc tgtgtgtgtg ccttgtcgag aaaaatcgga      840
agaacatgaa ttggcatctc tccccatata taaattatta ctttaaatta tatgatatgc      900
atgtagcata taaatgttta tattgttttt atatattata agttgacctt tatttattaa      960
acttcagcaa ccctacagta tataagcttt tttctcaata aaatcagtgt gcttgccttc     1020
```

<210> SEQ ID NO 8
<211> LENGTH: 257
<212> TYPE: PRT
<213> ORGANISM: Homo sapiens

<400> SEQUENCE: 8

```
Met Ser Ile Leu Phe Tyr Val Ile Phe Leu Ala Tyr Leu Arg Gly Ile
1               5                   10                  15

Gln Gly Asn Asn Met Asp Gln Arg Ser Leu Pro Glu Asp Ser Leu Asn
            20                  25                  30

Ser Leu Ile Ile Lys Leu Ile Gln Ala Asp Ile Leu Lys Asn Lys Leu
        35                  40                  45

Ser Lys Gln Met Val Asp Val Lys Glu Asn Tyr Gln Ser Thr Leu Pro
    50                  55                  60

Lys Ala Glu Ala Pro Arg Glu Pro Glu Arg Gly Gly Pro Ala Lys Ser
65                  70                  75                  80

Ala Phe Gln Pro Val Ile Ala Met Asp Thr Glu Leu Leu Arg Gln Gln
                85                  90                  95

Arg Arg Tyr Asn Ser Pro Arg Val Leu Leu Ser Asp Ser Thr Pro Leu
            100                 105                 110

Glu Pro Pro Pro Leu Tyr Leu Met Glu Asp Tyr Val Gly Ser Pro Val
        115                 120                 125

Val Ala Asn Arg Thr Ser Arg Arg Lys Arg Tyr Ala Glu His Lys Ser
    130                 135                 140

His Arg Gly Glu Tyr Ser Val Cys Asp Ser Glu Ser Leu Trp Val Thr
145                 150                 155                 160

Asp Lys Ser Ser Ala Ile Asp Ile Arg Gly His Gln Val Thr Val Leu
                165                 170                 175

Gly Glu Ile Lys Thr Gly Asn Ser Pro Val Lys Gln Tyr Phe Tyr Glu
            180                 185                 190

Thr Arg Cys Lys Glu Ala Arg Pro Val Lys Asn Gly Cys Arg Gly Ile
        195                 200                 205

Asp Asp Lys His Trp Asn Ser Gln Cys Lys Thr Ser Gln Thr Tyr Val
    210                 215                 220

Arg Ala Leu Thr Ser Glu Asn Asn Lys Leu Val Gly Trp Arg Trp Ile
225                 230                 235                 240

Arg Ile Asp Thr Ser Cys Val Cys Ala Leu Ser Arg Lys Ile Gly Arg
                245                 250                 255

Thr
```

<210> SEQ ID NO 9
<211> LENGTH: 1141
<212> TYPE: DNA
<213> ORGANISM: Homo sapiens

<400> SEQUENCE: 9

```
ccacactcag tctggcctcg gggcctttgc actggctgtg tccctgcct gtgatgccat      60
tctcctctgc ctggccaact cctacgttta ttcaagtctg gaccttgtca tcggctcctc    120
aggaaggcac tccgggaccc ccagatgggg gcggttccct gtgactcctg cacggaggc    180
caaccccttc cttgttcaat ggttccttga gggaccattc ccatgtgatt atcgaccatt    240
cggcaggcgt tcaaagtcaa aggccccaca ctgagtcctg cccagcgcc ctgtgcccgt     300
tggctgctgg agggacagac ggggcgtgcg gctgaccatc ccgtgcccgc aggctgagga    360
tgcagcgctg gaaggcggcg gccttggcct cagtgctctg cagctccgtg ctgtccatct    420
ggatgtgtcg agagggcctg cttctcagcc accgcctcgg acctgcgctg gtcccctgc    480
accgcctgcc tcgaaccctg gacgcccgga ttgcccgcct ggcccagtac cgtgcactcc    540
tgcaggggc cccggatgcg atggagctgc gcgagctgac gccctgggct gggcggcccc    600
caggtccgcg ccgtcgggcg gggccccggc ggcggcgcgc gcgtgcgcgg ttggggcgc    660
ggccttgcgg gctgcgcgag ctggaggtgc gcgtgagcga gctgggcctg gctacgcgt    720
ccgacgagac ggtgctgttc cgctactgcg caggcgcctg cgaggctgcc gcgcgcgtct    780
acgacctcgg gctgcgacga ctgcgccagc ggcggcgcct cgcggcggag cgggtgcgcg    840
cgcagccctg ctgccgcccg acggcctacg aggacgaggt gtccttcctg gacgcgcaca    900
gccgctacca cacggtgcac gagctgtcgg cgcgcgagtg cgcctgcgtg tgaccctacc    960
tcactcggcc ggcgcggcgg ccactccccc cgcctcgacg caccactgg ccggccccgc   1020
gaaagactgc gcgtgcgtag agcacgccgg cgcggcccg ggactctcgc gataactgta   1080
ctgagataaa gtgtggcaac tcgaaaaaa aaaaaaaaaa aaaaaaaaa aaaaaaaaa     1140
a                                                                  1141
```

<210> SEQ ID NO 10
<211> LENGTH: 197
<212> TYPE: PRT
<213> ORGANISM: Homo sapiens

<400> SEQUENCE: 10

```
Met Gln Arg Trp Lys Ala Ala Ala Leu Ala Ser Val Leu Cys Ser Ser
1               5                   10                  15

Val Leu Ser Ile Trp Met Cys Arg Glu Gly Leu Leu Leu Ser His Arg
            20                  25                  30

Leu Gly Pro Ala Leu Val Pro Leu His Arg Leu Pro Arg Thr Leu Asp
        35                  40                  45

Ala Arg Ile Ala Arg Leu Ala Gln Tyr Arg Ala Leu Leu Gln Gly Ala
    50                  55                  60

Pro Asp Ala Met Glu Leu Arg Glu Leu Thr Pro Trp Ala Gly Arg Pro
65                  70                  75                  80

Pro Gly Pro Arg Arg Arg Ala Gly Pro Arg Arg Arg Ala Arg Ala
                85                  90                  95

Arg Leu Gly Ala Arg Pro Cys Gly Leu Arg Glu Leu Glu Val Arg Val
            100                 105                 110

Ser Glu Leu Gly Leu Gly Tyr Ala Ser Asp Glu Thr Val Leu Phe Arg
```

```
              115                 120                 125
Tyr Cys Ala Gly Ala Cys Glu Ala Ala Arg Val Tyr Asp Leu Gly
        130                 135                 140

Leu Arg Leu Arg Gln Arg Arg Leu Arg Glu Arg Val Arg
145                 150                 155                 160

Ala Gln Pro Cys Cys Arg Pro Thr Ala Tyr Glu Asp Glu Val Ser Phe
                165                 170                 175

Leu Asp Ala His Ser Arg Tyr His Thr Val His Glu Leu Ser Ala Arg
                180                 185                 190

Glu Cys Ala Cys Val
        195

<210> SEQ ID NO 11
<211> LENGTH: 1404
<212> TYPE: DNA
<213> ORGANISM: Homo sapiens

<400> SEQUENCE: 11
cttgtcaccc aggtggcagg ggagtggtgc actctctgct cactgcaacc tcggcctcct      60
gggttcgagt gattctccta cctcagccta ctgagtagct gggattacag gcgtgcagca     120
ctatgcccgg ttaattttgg tattttttggt agagatgagg tttcaccatg ttgaccagct     180
gctctggaac tcctgacctc aagtcatcca cctgcctcag cctcccagag tgctgggatt     240
agaggtgtgg ggcacagtgc ctggcctgta gtagttgaat atttattatt aatctacaag     300
ttgcgcatta cgcaagccct agatataggg tcccccaaac ttctagaaca agggcttccc     360
cacaatcctg gcaggcaagc ctcccctggg gttcccaact tctttcccca ctgaagtttt     420
tacccccttc tctaatccca gcctccctct ttctgtctcc aggtgctccg agagatgctc     480
cctctcccct catgctccct cccatcctc ctccttttcc tcctcccag tgtgccaatt     540 gagtcccaac cccaccctc aacattgccc cttttctgg ccctgagtg ggaccttctc     600 tcccccgag tagtcctgtc tagggggtgcc cctgctgggc cccctctgct cttcctgctg     660
gaggctgggg cctttcggga gtcagcaggt gccccggcca accgcagccg gcgtggggtg     720
agcgaaactg caccagcgag tcgtcggggt gagctggctg tgtgcgatgc agtcagtggc     780
tgggtgacag accgccggac cgctgtggac ttgcgtgggc gcgaggtgga ggtgttgggc     840
gaggtgcctg cagctggcgg cagtcccctc cgccagtact tctttgaaac ccgctgcaag     900
gctgataacg ctgaggaagg tggcccgggg gcaggtggag ggggctgccg gggagtggac     960
aggaggcact gggtatctga gtgcaaggcc aagcagtcct atgtgcgggc attgaccgct    1020
gatgcccagg gccgtgtggg ctggcgatgg attcgaattg acactgcctg cgtctgcaca    1080
ctcctcagcc ggactggccg ggcctgagac ccatgcccag gaaaataaca gagctggatg    1140
ctgagagacc tcagggatgg cccagctgat ctaaggaccc cagtttggga actcatcaaa    1200
taatcacaaa atcacaattc tctgattttg agctcaatct ctgcaggatg ggtgaaacca    1260
catggggttt tggaggttga ataggagttc tcctggagca acttgagggt aataatgatg    1320
atgatataat aataatagcc actatttact gagtgtttac tgtttcttat ccctaataca    1380
taactcctca gatcaactct catg                                           1404

<210> SEQ ID NO 12
<211> LENGTH: 210
<212> TYPE: PRT
<213> ORGANISM: Homo sapiens
```

<400> SEQUENCE: 12

```
Met Leu Pro Leu Pro Ser Cys Ser Leu Pro Ile Leu Leu Phe Leu
1               5                   10                  15

Leu Pro Ser Val Pro Ile Glu Ser Gln Pro Pro Ser Thr Leu Pro
            20                  25                  30

Pro Phe Leu Ala Pro Glu Trp Asp Leu Leu Ser Pro Arg Val Leu
        35                  40                  45

Ser Arg Gly Ala Pro Ala Gly Pro Pro Leu Leu Phe Leu Leu Glu Ala
50                      55                      60

Gly Ala Phe Arg Glu Ser Ala Gly Ala Pro Ala Asn Arg Ser Arg
65              70                      75                  80

Gly Val Ser Glu Thr Ala Pro Ala Ser Arg Arg Gly Glu Leu Ala Val
                85                      90                      95

Cys Asp Ala Val Ser Gly Trp Val Thr Asp Arg Arg Thr Ala Val Asp
                100                     105                     110

Leu Arg Gly Arg Glu Val Glu Val Leu Gly Glu Val Pro Ala Ala Gly
                115                     120                     125

Gly Ser Pro Leu Arg Gln Tyr Phe Phe Glu Thr Arg Cys Lys Ala Asp
130                     135                     140

Asn Ala Glu Glu Gly Gly Pro Gly Ala Gly Gly Gly Cys Arg Gly
145                 150                     155                     160

Val Asp Arg Arg His Trp Val Ser Glu Cys Lys Ala Lys Gln Ser Tyr
                    165                     170                     175

Val Arg Ala Leu Thr Ala Asp Ala Gln Gly Arg Val Gly Trp Arg Trp
                180                     185                     190

Ile Arg Ile Asp Thr Ala Cys Val Cys Thr Leu Leu Ser Arg Thr Gly
                195                     200                     205

Arg Ala
    210
```

<210> SEQ ID NO 13
<211> LENGTH: 471
<212> TYPE: DNA
<213> ORGANISM: Homo sapiens

<400> SEQUENCE: 13

```
atggccgtag ggaagttcct gctgggctct ctgctgctcc tgtccctgca gctgggacag      60
ggctggggcc ccgatgcccg tggggttccc gtggccgatg agagttctc gtctgaacag      120
gtggcaaagg ctggagggac ctggctgggc acccaccgcc cccttgcccg cctgcgccga     180
gccctgtctg gtccatgcca gctgtggagc ctgaccctgt ccgtggcaga gctaggcctg     240
ggctacgcct cagaggagaa ggtcatcttc cgctactgcg ccggcagctg cccccgtggt     300
gcccgcaccc agcatggcct ggcgctggcc cggctgcagg gcagggccg agcccacggt      360
gggccctgct gccggcccac tcgctacacc gacgtggcct tcctcgatga ccgccaccgc     420
tggcagcggc tgcccagct ctcggcggct gcctgcggct gtggtggctg a               471
```

<210> SEQ ID NO 14
<211> LENGTH: 156
<212> TYPE: PRT
<213> ORGANISM: Homo sapiens

<400> SEQUENCE: 14

```
Met Ala Val Gly Lys Phe Leu Leu Gly Ser Leu Leu Leu Leu Ser Leu
1               5                   10                  15
```

```
Gln Leu Gly Gln Gly Trp Gly Pro Asp Ala Arg Val Pro Val Ala
            20                  25                  30

Asp Gly Glu Phe Ser Ser Glu Gln Val Ala Lys Ala Gly Gly Thr Trp
            35                  40                  45

Leu Gly Thr His Arg Pro Leu Ala Arg Leu Arg Arg Ala Leu Ser Gly
    50                  55                  60

Pro Cys Gln Leu Trp Ser Leu Thr Leu Ser Val Ala Glu Leu Gly Leu
65                  70                  75                  80

Gly Tyr Ala Ser Glu Glu Lys Val Ile Phe Arg Tyr Cys Ala Gly Ser
                85                  90                  95

Cys Pro Arg Gly Ala Arg Thr Gln His Gly Leu Ala Leu Ala Arg Leu
            100                 105                 110

Gln Gly Gln Gly Arg Ala His Gly Gly Pro Cys Cys Arg Pro Thr Arg
        115                 120                 125

Tyr Thr Asp Val Ala Phe Leu Asp Asp Arg His Arg Trp Gln Arg Leu
    130                 135                 140

Pro Gln Leu Ser Ala Ala Ala Cys Gly Cys Gly Gly
145                 150                 155
```

<210> SEQ ID NO 15
<211> LENGTH: 1652
<212> TYPE: DNA
<213> ORGANISM: Homo sapiens

<400> SEQUENCE: 15

```
ctctgagctt ctctgagcct tgtttgctca tctggaaaaa ggggattaaa ccatttacct      60
catggagttg tgaaagaata gctgcaaagc acctaacaca tagtaaggtt cccagtgcag     120
ctacttctgc tgggttgagt ctagctgtgt aggccccttg ttcctcacct ggagaaactg     180
gggtggcagg ccggtccccc acaaaagata actcatctct taatttgcaa gctgcctcaa     240
caggagggtg ggggaacagc tcaacaatgg ctgatgggcg ctcctggtgt tgatagagat     300
ggaacttgga cttggaggcc tctccacgct gtcccactgc ccctggccta gcggcaggt     360
gagtggttct cccagtgact cctacctggt actgaggaaa gcggcttga ctggtgaggg     420
agagcagggc ttggcttggg cagcggttag gtgtgggagg gaaaatggtc agggagggac     480
caggtgaatg ggaggaggag cgggacttct ctgaatggtc ggtgcactca ggtgattcct     540
cccctgggct cccagaggca gcaaaccat tatactggaa cctaggccct tcctgagttt     600
cccctccaca cagctaggag cccatgcccg gcctgatctc agcccgagga cagcccctcc     660
ttgaggtcct tctccccaa gcccacctgg gtgccctctt tctccctgag ctccacttg     720
gtctctccgc gcagcctgcc ctgtggccca cctggccgc tctggctctg ctgagcagcg     780
tcgcagaggc tccctgggc tccgcgcccc gcagccctgc ccccgcgaa gcccccgc       840
ctgtcctggc gtccccgcc ggccacctgc cgggtaggtg agagggcgag gggcggggc     900
ggggctggcc cgggacaccg cgcgtgactg gtctcattc cagggggacg cacgcccgc      960
tggtgcagtg gaagagcccg gcggccgccg ccgcagcctt ctcggcccgc gccccgccg    1020
cctgcacccc catctgctct tcccgcgggg ggcgcgcgg cgcgggctgg ggcccgggc    1080
agccgcgctc gggcagcggg ggcgcgggc tgccgcctgc gctcgcagct ggtgccggtg    1140
cgcgcgctcg gcctgggcca ccgctccgac gagctggtgc gtttccgctt ctgcagcggc   1200
tcctgccgcc gcgcgcgctc tccacacgac ctcagcctgg ccagcctact gggcgccggg    1260
gccctgcgac cgccccgggg ctcccggccc gtcagccagc cctgctgccg acccacgcgc   1320
```

| tacgaagcgg tctccttcat ggacgtcaac agcacctgga gaaccgtgga ccgcctctcc | 1380 |
| gccaccgcct gcggctgcct gggctgaggg ctcgctccag ggctttgcag actggaccct | 1440 |
| taccggtggc tcttcctgcc tgggaccctc ccgcagagtc ccactagcca gcggcctcag | 1500 |
| ccagggacga aggcctcaaa gctgagaggc ccctgccggt gggtgatgga tatcatcccc | 1560 |
| gaacaggtga agggacaact gactagcagc cccagagccc tcaccctgcg gatcccagcc | 1620 |
| taaaagacac cagagacctc agctatggag cc | 1652 |

<210> SEQ ID NO 16
<211> LENGTH: 237
<212> TYPE: PRT
<213> ORGANISM: Homo sapiens

<400> SEQUENCE: 16

Met Pro Gly Leu Ile Ser Ala Arg Gly Gln Pro Leu Leu Glu Val Leu
1               5                   10                  15

Pro Pro Gln Ala His Leu Gly Ala Leu Phe Leu Pro Glu Ala Pro Leu
            20                  25                  30

Gly Leu Ser Ala Gln Pro Ala Leu Trp Pro Thr Leu Ala Ala Leu Ala
        35                  40                  45

Leu Leu Ser Ser Val Ala Glu Ala Ser Leu Gly Ser Ala Pro Arg Ser
    50                  55                  60

Pro Ala Pro Arg Glu Gly Pro Pro Val Leu Ala Ser Pro Ala Gly
65                  70                  75                  80

His Leu Pro Gly Gly Arg Thr Ala Arg Trp Cys Ser Gly Arg Ala Arg
                85                  90                  95

Arg Pro Pro Pro Gln Pro Ser Arg Pro Ala Pro Pro Pro Ala Pro
            100                 105                 110

Pro Ser Ala Leu Pro Arg Gly Gly Arg Ala Ala Arg Ala Gly Gly Pro
        115                 120                 125

Gly Ser Arg Ala Arg Ala Ala Gly Ala Arg Gly Cys Arg Leu Arg Ser
    130                 135                 140

Gln Leu Val Pro Val Arg Ala Leu Gly Leu Gly His Arg Ser Asp Glu
145                 150                 155                 160

Leu Val Arg Phe Arg Phe Cys Ser Gly Ser Cys Arg Arg Ala Arg Ser
                165                 170                 175

Pro His Asp Leu Ser Leu Ala Ser Leu Leu Gly Ala Gly Ala Leu Arg
            180                 185                 190

Pro Pro Pro Gly Ser Arg Pro Val Ser Gln Pro Cys Cys Arg Pro Thr
        195                 200                 205

Arg Tyr Glu Ala Val Ser Phe Met Asp Val Asn Ser Thr Trp Arg Thr
    210                 215                 220

Val Asp Arg Leu Ser Ala Thr Ala Cys Gly Cys Leu Gly
225                 230                 235

<210> SEQ ID NO 17
<211> LENGTH: 1914
<212> TYPE: DNA
<213> ORGANISM: Homo sapiens

<400> SEQUENCE: 17

| agagtcacat ctcttatttg gaccagtata gacagaagta aacccagctg acttgtttcc | 60 |
| tgggacagtt gagttaaggg atggctttca cagagcattc accgctgacc cctcaccgtc | 120 |
| gggacctctg tagccgctct atctggctag caaggaagat tcgttcagac ctgactgctc | 180 |

```
ttacggaatc ctatgtgaag catcagggcc tgaacaagaa catcaacctg gactctgcgg    240
atgggatgcc agtggcaagc actgatcagt ggagtgagct gaccgaggca gagcgactcc    300
aagagaacct tcaagcttat cgtaccttcc atgttttgtt ggccaggctc ttagaagacc    360
agcaggtgca ttttacccca accgaaggtg acttccatca agctatacat acccttcttc    420
tccaagtcgc tgcctttgca taccagatag aggagttaat gatactcctg aatacaaga    480 tcccccgcaa tgaggctgat gggatgccta ttaatgttgg agatggtggt ctctttgaga    540
agaagctgtg gggcctaaag gtgctgcagg agctttcaca gtggacagta aggtccatcc    600
atgaccttcg tttcatttct tctcatcaga ctgggatccc agcacgtggg agccattata    660
ttgctaacaa caagaaaatg tagcagttag tcccttctct cttccttgct ttctcttcta    720
atggaatatg cgtagttccc tggggcctcg ctttcccatc ttaaatttct aaaaacagtt    780
aagacaacag gcattttctt tcttttttct ctgaccacct gcagcctgtt gaaggactac    840
aggtattttc atcaagtagc gttggagaca tacacaaatg gcatacaag tttagcctgg    900 ggggtgtgat tgtgtgcgt gcttgcatgt gctgcaggtg taagagagtg ggagcaggga    960
caacgtcctt ccacttcagg gttctaacct ttctaaccca ctaagtaacc tctacaggca   1020
tttaactgcc ttacagacag aatatacata tgttaattct agtcctggat gactcggtct   1080
gagaagattc aatttaaaat cagactcttt agttgattta aactcttaga gaataagaat   1140
aataatggct aacttttatt atcttctata ttaaggcagt atgccaaggg tctttatgta   1200
tattatgtac agcgtttaca accttgtgag caaggtggtg ttactcccat taggtagatg   1260
agaaaacagg ctcacagaga tttggttaag ctcacacagc taacaagtag cacactgagt   1320
ttgaacacag atcattctcc ttgtaaaagc ctatgtgcct ttcactttag aggcttgatc   1380
atgaatcact gcacctcttt gtcacagggt gttggaagat gcatccatgt aatctattcc   1440
catcgctgga aaacagctgc tgttagatgt cctcagaagt cagttgcaaa ttttagcgtt   1500
aaagtcagga tttattgttc atacttggcg gtgaggaggg cagctggaga tcttaagatt   1560 ccatttgga aatgattag gcccgccaaa cttctgaact ttggaagctg gggatgttta   1620
gtaatacagc ctggttttta agtactcact aaaagttctc aaatattggg ttgggcacgg   1680
cttataccag gttacctcac ttttaattag tgatgcaggc agtgtaaccc aagcatttgt   1740
ggacaatgag tggaatacta agttaaaaa gtcaaacttt cacctcagat tttctggact   1800
tagtcatgag gagagggtga ggcccactct gttcctactg gagataccag agactctgaa   1860
actatagaat aaagcctctg tgctgcacaa caaaaaaaaa aaaaaaaaaa aaaa          1914
```

<210> SEQ ID NO 18
<211> LENGTH: 200
<212> TYPE: PRT
<213> ORGANISM: Homo sapiens

<400> SEQUENCE: 18

```
Met Ala Phe Thr Glu His Ser Pro Leu Thr Pro His Arg Arg Asp Leu
1               5                   10                  15

Cys Ser Arg Ser Ile Trp Leu Ala Arg Lys Ile Arg Ser Asp Leu Thr
            20                  25                  30

Ala Leu Thr Glu Ser Tyr Val Lys His Gln Gly Leu Asn Lys Asn Ile
        35                  40                  45

Asn Leu Asp Ser Ala Asp Gly Met Pro Val Ala Ser Thr Asp Gln Trp
    50                  55                  60

Ser Glu Leu Thr Glu Ala Glu Arg Leu Gln Glu Asn Leu Gln Ala Tyr
```

```
              65                  70                  75                  80
Arg Thr Phe His Val Leu Leu Ala Arg Leu Leu Glu Asp Gln Gln Val
                        85                  90                  95

His Phe Thr Pro Thr Glu Gly Asp Phe His Gln Ala Ile His Thr Leu
                100                 105                 110

Leu Leu Gln Val Ala Ala Phe Ala Tyr Gln Ile Glu Leu Met Ile
            115                 120                 125

Leu Leu Glu Tyr Lys Ile Pro Arg Asn Glu Ala Asp Gly Met Pro Ile
        130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
                180                 185                 190

Tyr Ile Ala Asn Asn Lys Lys Met
            195                 200

<210> SEQ ID NO 19
<211> LENGTH: 7321
<212> TYPE: DNA
<213> ORGANISM: Homo sapiens

<400> SEQUENCE: 19
ttttgtagat aaatgtgagg attttctcta aatccctctt ctgtttgcta aatctcactg      60
tcactgctaa attcagagca gatagagcct gcgcaatgga ataaagtcct caaaattgaa     120
atgtgacatt gctctcaaca tctcccatct ctctggattt cttttgctt cattattcct      180 gctaaccaat tcattttcag actttgtact tcagaagcaa tgggaaaaat cagcagtctt     240
ccaacccaat tatttaagtg ctgcttttgt gatttcttga aggtgaagat gcacaccatg     300
tcctcctcgc atctcttcta cctggcgctg tgcctgctca ccttcaccag ctctgccacg     360
gctggaccgg agacgctctg cggggctgag ctggtggatg ctcttcagtt cgtgtgtgga     420
gacaggggct tttatttcaa caagcccaca gggtatggct ccagcagtcg agggcgcct      480 cagacaggca tcgtggatga gtgctgcttc cggagctgtg atctaaggag ctggagatg      540 tattgcgcac ccctcaagcc tgccaagtca gctcgctctg tccgtgccca gcgccacacc     600
gacatgccca gacccagaa ggaagtacat ttgaagaacg caagtagagg gagtgcagga     660
aacaagaact acaggatgta ggaagaccct cctgaggagt gaagagtgac atgccaccgc     720
aggatccttt gctctgcacg agttacctgt taaactttgg aacacctacc aaaaaataag    780
tttgataaca tttaaaagat gggcgttttcc cccaatgaaa tacacaagta acattccaa    840 cattgtcttt aggagtgatt tgcaccttgc aaaaatggtc ctggagttgg tagattgctg    900
ttgatctttt atcaataatg ttctatagaa agaaaaaaa aaatatatat atatatatat     960
cttagtccct gcctctcaag agccacaaat gcatgggtgt tgtatagatc cagttgcact   1020
aaattcctct ctgaatcttg gctgctggag ccattcattc agcaaccttg tctaagtggt   1080
ttatgaattg tttccttatt tgcacttctt tctacacaac tcgggctgtt tgttttacag   1140
tgtctgataa tcttgttagt ctatacccac cacctcccttt cataacctttt atatttgccg  1200 aatttggcct cctcaaaagc agcagcaagt cgtcaagaag cacaccaatt ctaacccaca   1260
agattccatc tgtggcattt gtaccaaata taagttggat gcattttatt ttagacacaa   1320
agctttattt ttccacatca tgcttacaaa aaagaataat gcaaatagtt gcaactttga   1380
```

```
ggccaatcat ttttaggcat atgttttaaa catagaaagt ttcttcaact caaaagagtt    1440
ccttcaaatg atgagttaat gtgcaaccta attagtaact ttcctctttt tattttttcc    1500
atatagagca ctatgtaaat ttagcatatc aattatacag gatatatcaa acagtatgta    1560
aaactctgtt ttttagtata atggtgctat tttgtagttt gttatatgaa agagtctggc    1620
caaaacggta atacgtgaaa gcaaaacaat aggggaagcc tggagccaaa gatgacacaa    1680
ggggaagggt actgaaaaca ccatccattt gggaaagaag gcaaagtccc cccagttatg    1740
ccttccaaga ggaacttcag acacaaaagt ccactgatgc aaattggact ggcgagtcca    1800
gagaggaaac tgtggaatgg aaaaagcaga aggctaggaa ttttagcagt cctggtttct    1860
ttttctcatg gaagaaatga acatctgcca gctgtgtcat ggactcacca ctgtgtgacc    1920
ttgggcaagt cacttcacct ctctgtgcct cagtttcctc atctgcaaaa tgggggcaat    1980
atgtcatcta cctacctcaa aggggtggta taaggtttaa aaagataaag attcagattt    2040 tttttacccct gggttgctgt aagggtgcaa catcagggcg cttgagttgc tgagatgcaa    2100
ggaattctat aaataaccca ttcatagcat agctagagat tggtgaattg aatgctcctg    2160
acatctcagt tcttgtcagt gaagctatcc aaataactgg ccaactagtt gttaaaagct    2220
aacagctcaa tctcttaaaa cacttttcaa aatatgtggg aagcatttga ttttcaattt    2280
gattttgaat tctgcatttg gttttatgaa tacaaagata agtgaaaaga gagaaaggaa    2340
aagaaaaagg agaaaaacaa agagatttct accagtgaaa ggggaattaa ttactctttg    2400
ttagcactca ctgactcttc tatgcagtta ctacatatct agtaaaacct cgtttaatac    2460
tataaataat attctattca ttttgaaaaa cacaatgatt ccttcttttc taggcaatat    2520
aaggaaagtg atccaaaatt tgaaatatta aaataatatc taataaaaag tcacaaagtt    2580
atcttcttta acaaacttta ctcttattct tagctgtata tacatttttt taaaagtttg    2640
ttaaaatatg cttgactaga gtttccagtt gaaaggcaaa aacttccatc acaacaagaa    2700
atttcccatg cctgctcaga agggtagccc ctagctctct gtgaatgtgt tttatccatt    2760
caactgaaaa ttggtatcaa gaaagtccac tggttagtgt actagtccat catagcctag    2820
aaaatgatcc ctatctgcag atcaagattt tctcattaga acaatgaatt atccagcatt    2880
cagatctttc tagtcacctt agaacttttt ggttaaaagt acccaggctt gattatttca    2940
tgcaaattct atattttaca ttcttggaaa gtctatatga aaaacaaaaa taacatcttc    3000 agttttctc ccactgggtc acctcaagga tcagaggcca ggaaaaaaaa aaaaaagact    3060
ccctggatct ctgaatatat gcaaaaagaa ggccccattt agtggagcca gcaatcctgt    3120
tcagtcaaca agtatttaa ctctcagtcc aacattattt gaattgagca cctcaagcat    3180
gcttagcaat gttctaatca ctatggacag atgtaaaaga aactatacat catttttgcc    3240
ctctgcctgt tttccagaca tacaggttct gtggaataag atactggact cctcttccca    3300
agatggcact tcttttttatt tcttgtcccc agtgtgtacc ttttaaaatt attccctctc    3360
aacaaaactt tataggcagt cttctgcaga cttaacgtgt tttctgtcat agttagatgt    3420
gataattcta agagtgtcta tgacttattt ccttcactta attctatcca cagtcaaaaa    3480
tcccccaagg aggaaagctg aaagatgcac tgccatatta tctttcttaa cttttttccaa    3540 cacataatcc tctccaactg gattataaat aaattgaaaa taactcatta taccaattca    3600 ctatttttatt ttttaatgaa ttaaaactag aaaacaaatt gatgcaaacc ctggaagtca    3660
gttgattact atatactaca gcagaatgac tcagatttca tagaaaggag caaccaaaat    3720
```

```
gtcacaaccc aaaactttac aagctttgct tcagaattag attgctttat aattcttgaa    3780
tgaggcaatt tcaagatatt tgtaaaagaa cagtaaacat tggtaagaat gagctttcaa    3840
ctcataggct tatttccaat ttaattgacc atactggata cttaggtcaa atttctgttc    3900
tctcttcccc aaataatatt aaagtattat ttgaactttt taagatgagg cagttcccct    3960
gaaaaagtta atgcagctct ccatcagaat ccactcttct agggatatga aaatctctta    4020
acacccaccc tacatacaca gacacacaca cacacacaca cacacacaca cacacacaca    4080
ttcaccctaa ggatccaatg aatactgaa  agaaatcac  ttccttgaaa  attttattaa    4140
aaaacaaaca aacaaacaaa aagcctgtcc acccttgaga atccttcctc tccttggaac    4200
gtcaatgttt gtgtagatga aaccatctca tgctctgtgg ctccagggtt tctgttacta    4260
ttttatgcac ttgggagaag gcttagaata aaagatgtag cacattttgc tttcccattt    4320
attgtttggc cagctatgcc aatgtggtgc tattgtttct ttaagaaagt acttgactaa    4380
aaaaaaaaga aaaaagaaa  aaaaagaaag catagacata ttttttttaaa gtataaaaac    4440 aacaattcta tagatagatg gcttaataaa atagcattag gtctatctag ccaccaccac    4500
ctttcaactt tttatcactc acaagtagtg tactgttcac caaattgtga atttgggggt    4560
gcaggggcag gagttggaaa ttttttaaag ttagaaggct ccattgtttt gttggctctc    4620
aaacttagca aaattagcaa tatattatcc aatcttctga acttgatcaa gagcatggag    4680
aataaacgcg ggaaaaaaga tcttataggc aaatagaaga atttaaaaga taagtaagtt    4740
ccttattgat ttttgtgcac tctgctctaa aacagatatt cagcaagtgg agaaaataag    4800
aacaaagaga aaaaatacat agatttacct gcaaaaaata gcttctgcca aatccccctt    4860
gggtattctt tggcatttac tggtttatag aagacattct cccttcaccc agacatctca    4920
aagagcagta gctctcatga aaagcaatca ctgatctcat ttgggaaatg ttggaaagta    4980
tttccttatg agatgggggt tatctactga taaagaaaga atttatgaga aattgttgaa    5040
agagatggct aacaatctgt gaagattttt tgtttcttgt ttttgttttt ttttttttt     5100 tactttatac agtctttatg aatttcttaa tgttcaaaat gacttggttc ttttcttctt    5160
tttttatatc agaatgagga ataataagtt aaacccacat agactcttta aaactatagg    5220
ctagatagaa atgtatgttt gacttgttga agctataatc agactattta aaatgttttg    5280 ctattttttaa tcttaaaaga ttgtgctaat ttattagagc agaacctgtt tggctctcct    5340
cagaagaaag aatctttcca ttcaaatcac atggctttcc accaatattt tcaaaagata    5400
aatctgattt atgcaatggc atcatttatt ttaaaacaga agaattgtga agtttatgc     5460 ccctcccttg caaagaccat aaagtccaga tctggtaggg gggcaacaac aaaaggaaaa    5520
tgttgttgat tctggttttt ggattttgtt ttgttttcaa tgctagtgtt taatcctgta    5580
gtacatattt gcttattgct attttaatat tttataagac cttcctgtta ggtattagaa    5640
agtgatacat agatatcttt tttgtgtaat ttctatttaa aaaagagaga agactgtcag    5700
aagctttaag tgcatatggt acaggataaa gatatcaatt taaataacca attcctatct    5760
ggaacaatgc ttttgttttt taagaaaacc tctcacagat aagacagagg cccaggggat    5820
ttttgaagct gtcttattc  tgcccccatc ccaacccagc ccttattatt ttagtatctg    5880
cctcagaatt ttatagaggg ctgaccaagc tgaaactcta gaattaaagg aacctcactg    5940
aaaacatata tttcacgtgt tccctctttt ttttttttcct ttttgtgaga tggggtctcg    6000
cactgtcccc caggctggag tgcagtggca tgatctcggc tcactgcaac ctccacctcc    6060
tgggtttaag cgattctcct gcctcagcct cctgagtagc tgggattaca ggcacccacc    6120
```

```
actatgcccg gctaatttt tggatttta atagagacgg ggttttacca tgttggccag    6180
gttggtctca aactcctgac cttgtgattt gcccgcctca gcctcccaaa ttgctgggat    6240
tacaggcatg agccaccaca ccctgcccat gtgttccctc ttaatgtatg attacatgga    6300
tcttaaacat gatccttctc tcctcattct tcaactatct ttgatggggt ctttcaaggg    6360
gaaaaaaatc caagcttttt taaagtaaaa aaaaaaaag agaggacaca aaaccaaatg    6420
ttactgctca actgaaatat gagttaagat ggagacagag tttctcctaa taaccggagc    6480
tgaattacct ttcactttca aaaacatgac cttccacaat ccttagaatc tgccttttt     6540 tatattactg aggcctaaaa gtaaacatta ctcatttat tttgcccaaa atgcactgat    6600
gtaaagtagg aaaaataaaa acagagctct aaaatccctt tcaagccacc cattgacccc    6660
actcaccaac tcatagcaaa gtcacttctg ttaatccctt aatctgattt tgtttggata    6720
tttatcttgt acccgctgct aaacacactg caggagggac tctgaaacct caagctgtct    6780
acttacatct tttatctgtg tctgtgtatc atgaaaatgt ctattcaaaa tatcaaaacc    6840
tttcaaatat cacgcagctt atattcagtt tacataaagg ccccaaatac catgtcagat    6900 cttttggta aaagagttaa tgaactatga gaattgggat tacatcatgt attttgcctc    6960
atgtattttt atcacactta taggccaagt gtgataaata aacttacaga cactgaatta    7020
atttcccctg ctactttgaa accagaaaat aatgactggc cattcgttac atctgtctta    7080
gttgaaaagc atatttta ttaaattaat tctgattgta tttgaaatta ttattcaatt    7140
cacttatggc agaggaatat caatcctaat gacttctaaa aatgtaacta attgaatcat    7200
tatcttacat ttactgttta ataagcatat tttgaaaatg tatggctaga gtgtcataat    7260
aaaatggtat atctttcttt agtaattaca ttaaaattag tcatgtttga ttaattagtt    7320
c                                                                    7321
```

<210> SEQ ID NO 20
<211> LENGTH: 153
<212> TYPE: PRT
<213> ORGANISM: Homo sapiens

<400> SEQUENCE: 20

```
Met Gly Lys Ile Ser Ser Leu Pro Thr Gln Leu Phe Lys Cys Cys Phe
1               5                  10                  15

Cys Asp Phe Leu Lys Val Lys Met His Thr Met Ser Ser His Leu
                20                  25                  30

Phe Tyr Leu Ala Leu Cys Leu Leu Thr Phe Thr Ser Ser Ala Thr Ala
            35                  40                  45

Gly Pro Glu Thr Leu Cys Gly Ala Glu Leu Val Asp Ala Leu Gln Phe
        50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Thr Gln Lys Glu Val His Leu Lys Asn Ala Ser Arg Gly
130                 135                 140

Ser Ala Gly Asn Lys Asn Tyr Arg Met
```

145             150

<210> SEQ ID NO 21
<211> LENGTH: 1892
<212> TYPE: DNA
<213> ORGANISM: Homo sapiens

<400> SEQUENCE: 21

| | | | | | |
|---|---|---|---|---|---|
| actggccgct | gagagaagaa | tcgggtggag | cagagagcag | ctgctgcagg gcagacagcc | 60 |
| ggacccccaa | atctgcacgt | accagcagtc | agccgcccca | cgcagggacc ggcttacccc | 120 |
| tcgctccccg | ccctcactca | ctttctcccg | ccctcggccc | ggcctcccag ctctctactt | 180 |
| cgcgtgtcta | caaactcaac | tcccggtttc | cgtgcctctc | caccgctcga gttctctact | 240 |
| ctccatatcc | gagggcccc | tcccagcatc | taccccctc | ccaacctcgg ggacctagc | 300 |
| caagctaggg | gggactggat | ccgacgggtg | gagcagccag | gtgagccccg aaaggtgggg | 360 |
| cggggcaggg | gcgctcccag | ccccaccccg | ggatctggtg | acgctggggc tggaatttga | 420 |
| caccggacgg | ctgcggcggc | gggcaggagg | ctgctgaggg | atggagttgg gcccggcccc | 480 |
| cagacaaggc | cgggggctc | cgccagcagc | aggtccctcg | gccccagcc ctcgctgcca | 540 |
| cccgggcctg | gagccccaca | cccgagggtg | cagactggct | gccaaggcca cttttggc | 600 |
| taaaagaggc | actgccaggt | gtacagtcct | gggcatgcgc | tgtttgagct tcggggaga | 660 |
| gcccagcact | ggtccccgga | aaggtgccta | gaagaacaag | gtgcaggacc ccgtgctgcc | 720 |
| tcaacaggag | ggtgggggaa | cagctcaaca | atggctgatg | ggcgctcctg gtgttgatag | 780 |
| agatggaact | tggacttgga | ggcctctcca | cgctgtccca | ctgcccctgg cctaggcggc | 840 |
| agcctgccct | gtggcccacc | ctggccgctc | tggctctgct | gagcagcgtc gcagaggcct | 900 |
| ccctgggctc | cgcgccccgc | agccctgccc | ccgcgaagg | cccccgcct gtcctggcgt | 960 |
| cccccgccgg | ccacctgccg | ggggacgca | cggcccgctg | gtgcagtgga agagcccggc | 1020 |
| ggccgccgcc | gcagccttct | cggcccgcgc | cccgccgcc | tgcaccccca tctgctcttc | 1080 |
| cccgcggggg | ccgcgcggcg | cgggctgggg | gcccgggcag | ccgcgctcgg gcagcggggg | 1140 |
| cgcggggctg | ccgcctgcgc | tcgcagctgg | tgccggtgcg | cgcgctcggc ctgggccacc | 1200 |
| gctccgacga | gctggtgcgt | ttccgcttct | gcagcggctc | ctgccgccgc gcgcgctctc | 1260 |
| cacacgacct | cagcctggcc | agcctactgg | gcgccggggc | cctgcgaccg cccccggggct | 1320 |
| cccggcccgt | cagccagccc | tgctgccgac | ccacgcgcta | cgaagcggtc tccttcatgg | 1380 |
| acgtcaacag | cacctggaga | accgtggacc | gcctctccgc | caccgcctgc ggctgcctgg | 1440 |
| gctgagggct | cgctccaggg | ctttgcagac | tggaccctta | ccggtggctc ttcctgcctg | 1500 |
| ggaccctccc | gcagagtccc | actagccagc | ggcctcagcc | agggacgaag gcctcaaagc | 1560 |
| tgagaggccc | ctaccggtgg | gtgatggata | tcatccccga | acaggtgaag ggacaactga | 1620 |
| ctagcagccc | cagagccctc | accctgcgga | tcccagccta | aaagacacca gagacctcag | 1680 |
| ctatggagcc | cttcggaccc | acttctcaca | gactctggca | ctggcaggc ctcgaacctg | 1740 |
| ggacccctcc | tctgatgaac | actacagtgg | ctgaggcatc | agcccccgcc caggccctgt | 1800 |
| agggacagca | tttgaaggac | acatattgca | gttgcttggt | tgaaagtgcc tgtgctggaa | 1860 |
| ctggcctgta | ctcactcatg | ggagctggcc | cc | | 1892 |

<210> SEQ ID NO 22
<211> LENGTH: 220
<212> TYPE: PRT
<213> ORGANISM: Homo sapiens

<400> SEQUENCE: 22

```
Met Glu Leu Gly Leu Gly Gly Leu Ser Thr Leu Ser His Cys Pro Trp
1               5                   10                  15
Pro Arg Arg Gln Pro Ala Leu Trp Pro Thr Leu Ala Ala Leu Ala Leu
            20                  25                  30
Leu Ser Ser Val Ala Glu Ala Ser Leu Gly Ser Ala Pro Arg Ser Pro
        35                  40                  45
Ala Pro Arg Glu Gly Pro Pro Pro Val Leu Ala Ser Pro Ala Gly His
    50                  55                  60
Leu Pro Gly Gly Arg Thr Ala Arg Trp Cys Ser Gly Arg Ala Arg Arg
65                  70                  75                  80
Pro Pro Pro Gln Pro Ser Arg Pro Ala Pro Pro Pro Ala Pro Pro
                85                  90                  95
Ser Ala Leu Pro Arg Gly Gly Arg Ala Ala Arg Ala Gly Gly Pro Gly
                100                 105                 110
Ser Arg Ala Arg Ala Ala Gly Ala Arg Gly Cys Arg Leu Arg Ser Gln
            115                 120                 125
Leu Val Pro Val Arg Ala Leu Gly Leu Gly His Arg Ser Asp Glu Leu
        130                 135                 140
Val Arg Phe Arg Phe Cys Ser Gly Ser Cys Arg Arg Ala Arg Ser Pro
145                 150                 155                 160
His Asp Leu Ser Leu Ala Ser Leu Leu Gly Ala Gly Ala Leu Arg Pro
                165                 170                 175
Pro Pro Gly Ser Arg Pro Val Ser Gln Pro Cys Cys Arg Pro Thr Arg
                180                 185                 190
Tyr Glu Ala Val Ser Phe Met Asp Val Asn Ser Thr Trp Arg Thr Val
            195                 200                 205
Asp Arg Leu Ser Ala Thr Ala Cys Gly Cys Leu Gly
            210                 215                 220
```